US009661995B2

(12) United States Patent
Date et al.

(10) Patent No.: US 9,661,995 B2
(45) Date of Patent: May 30, 2017

(54) CAPSULE ENDOSCOPE SYSTEM, OPERATING METHOD OF IMAGE DISPLAY, AND COMPUTER-READABLE RECORDING MEDIUM

(71) Applicant: OLYMPUS CORPORATION, Tokyo (JP)

(72) Inventors: Rei Date, Musashino (JP); Katsuyoshi Taniguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 218 days.

(21) Appl. No.: 14/560,752

(22) Filed: Dec. 4, 2014

(65) Prior Publication Data

US 2015/0150437 A1 Jun. 4, 2015

Related U.S. Application Data

(60) Division of application No. 13/756,933, filed on Feb. 1, 2013, now abandoned, which is a continuation of
(Continued)

(30) Foreign Application Priority Data

Jul. 22, 2011 (JP) ................................. 2011-161322

(51) Int. Cl.
*G09G 5/00* (2006.01)
*A61B 1/00* (2006.01)
(Continued)

(52) U.S. Cl.
CPC ............ *A61B 1/041* (2013.01); *A61B 1/0005* (2013.01); *A61B 1/00006* (2013.01);
(Continued)

(58) Field of Classification Search
CPC ..... A61B 1/041; A61B 1/0005; A61B 5/7445; A61B 2034/2074; G09G 5/14;
(Continued)

(56) References Cited

U.S. PATENT DOCUMENTS

2005/0043583 A1 2/2005 Killmann et al.
2006/0287463 A1 12/2006 Wehner
(Continued)

FOREIGN PATENT DOCUMENTS

EP 2008574 A1 12/2008
JP 2006288869 A * 10/2006
(Continued)

OTHER PUBLICATIONS

International Search Report dated Oct. 16, 2012 received in International Application No. PCT/JP2012/067489.
(Continued)

*Primary Examiner* — Matthew J Kasztejna
*Assistant Examiner* — Aaron B Fairchild
(74) *Attorney, Agent, or Firm* — Scully, Scott, Murphy & Presser, P.C.

(57) ABSTRACT

A capsule endoscope system includes: a capsule endoscope including a first and a second imaging units; an image display that displays images captured by the first and second imaging units; a control unit that determines a moving direction of the capsule endoscope during imaging, specifies one of the imaging units which faces the moving direction of the capsule endoscope during imaging, and determines the posture of the capsule endoscope; and a display control unit that generates a display screen, arranges the image captured by the imaging unit facing the moving direction in a first display region in the display screen, arranges the image captured by the other imaging unit in a second display region in the display screen, and changes the positions of the
(Continued)

first and second display regions according to the determination result of the position of the capsule endoscope.

6 Claims, 24 Drawing Sheets

Related U.S. Application Data application No. PCT/JP2012/067489, filed on Jul. 9, 2012.

(51) Int. Cl.

| | | |
|---|---|---|
| *A61B 1/04* | (2006.01) | |
| *G09G 5/14* | (2006.01) | |
| *A61B 1/05* | (2006.01) | |
| *A61B 5/00* | (2006.01) | |
| *A61B 1/045* | (2006.01) | |
| *A61B 5/07* | (2006.01) | |

(52) U.S. Cl.
CPC ...... *A61B 1/00009* (2013.01); *A61B 1/00016* (2013.01); *A61B 1/00156* (2013.01); *A61B 1/00181* (2013.01); *A61B 1/045* (2013.01); *A61B 1/05* (2013.01); *A61B 5/68* (2013.01); *G09G 5/14* (2013.01); *A61B 5/073* (2013.01); *G09G 2340/0464* (2013.01); *G09G 2340/0471* (2013.01)

(58) Field of Classification Search
CPC ... G09G 2340/0464; G09G 2340/0471; G09G 2340/0478
USPC .................................. 345/635, 672
See application file for complete search history.

(56) References Cited

U.S. PATENT DOCUMENTS

| | | |
|---|---|---|
| 2007/0118017 A1 | 5/2007 | Honda |
| 2007/0232870 A1 | 10/2007 | Mizuno |
| 2009/0043157 A1 | 2/2009 | Hirakawa et al. |
| 2010/0061597 A1 | 3/2010 | Kanda et al. |

FOREIGN PATENT DOCUMENTS

| | | |
|---|---|---|
| JP | 2007282794 A | 11/2007 |
| JP | 2008301877 A | 12/2008 |
| JP | 2009056205 A | 3/2009 |
| JP | 2009089910 A | 4/2009 |
| JP | 2009148468 A | 7/2009 |
| JP | 2010017555 A | 1/2010 |
| WO | 2006109370 A1 | 10/2006 |
| WO | 2007119784 A1 | 10/2007 |

OTHER PUBLICATIONS

Non-Final US Office Action dated Jan. 29, 2014 received in U.S. Appl. No. 13/756,933.
Final US Office Action dated Jun. 4,2014 received in U.S. Appl. No. 13/756,933.
Extended Supplementary European Search Report dated Nov. 17, 2014 received in Application No./Patent No. 12817079.2-1660 / 2684511 PCT/JP2012067489.

* cited by examiner (a)  (b)

(a)  (b)

(a)　　　　　　　　　　　(b)

(a)　　　　　　　　　　　(b)

(a) (b)

(a) (b)

(a) (b)

CAPSULE ENDOSCOPE SYSTEM, OPERATING METHOD OF IMAGE DISPLAY, AND COMPUTER-READABLE RECORDING MEDIUM

CROSS REFERENCES TO RELATED APPLICATIONS

This application is a divisional application of U.S. patent application Ser. No. 13/756,933, filed on Feb. 1, 2013, which is a continuation of PCT International Application No. PCT/JP2012/067489, filed on Jul. 9, 2012, which designates the United States, incorporated herein by reference, and which claims the benefit of priority from Japanese Patent Applications No. 2011-161322, filed on Jul. 22, 2011, incorporated herein by reference.

BACKGROUND OF THE INVENTION

1. Field of the Invention

The present invention relates to a capsule endoscope system, a method of operating an image display, and a computer-readable recording medium which display images acquired by a capsule endoscope introduced into a subject.

2. Description of the Related Art

In recent years, in the field of endoscopes, a swallow-type capsule endoscope has been developed. The capsule endoscope is introduced into the body of the subject (patient) from the mouth and sequentially captures the images of the lumens (alimentary canals), such as the esophagus, the stomach, the small intestine, and the large intestine, while is being moved in the lumens by the peristaltic motion until it is naturally eliminated from the subject. Image data generated from the image captured by the capsule endoscope is sequentially transmitted by wireless communication, is received by a receiving device which is provided outside the subject, and is then stored in a memory which is provided in the receiving device. The image data is transmitted to an image display after examination ends, predetermined image processing is performed on the image data, and the processed image data is displayed as an in-vivo image on a display. The user (for example, a doctor) observes the in-vivo image displayed on the display, finds an abnormality, and specifies the position (organ) of the abnormality in the subject. This process is referred to as observation.

As the capsule endoscope, the followings have been developed: a monocular capsule endoscope in which an imaging unit including an imaging element and an illumination element is provided on one side of a capsule in the longitudinal direction; and a pantoscopic (binocular) capsule endoscope in which imaging units are provided on both sides of a (for example, see Japanese Patent Application Laid-open No. 2009-89910, Japanese Patent Application Laid-open No. 2007-282794, Japanese Patent Application Laid-open No. 2006-288869, and Japanese Patent Application Laid-open No. 2010-17555). The pantoscopic capsule endoscope can capture images on the front and rear sides of the capsule in the longitudinal direction.

SUMMARY OF THE INVENTION

According to one aspect of the present invention, a capsule endoscope system includes: a capsule endoscope that includes a first imaging unit which captures an image in a first direction and a second imaging unit which captures an image in a second direction different from the first direction, is introduced into a subject, and captures an in-vivo image of the subject; an image display that displays an image based on image data obtained from the in-vivo images of the subject captured by the first and second imaging units; a control unit that determines a moving direction of the capsule endoscope during imaging, specifies one of the first and second imaging units which faces the moving direction of the capsule endoscope during imaging, and determines the position of the capsule endoscope; and a display control unit that generates a display screen including a first display region in which an image in the moving direction of the capsule endoscope is arranged and a second display region in which an image in a direction opposite to the moving direction of the capsule endoscope is arranged, arranges, in the first display region, an image based on the image data acquired by the imaging unit which is specified to face the moving direction by the control unit, arranges, in the second display region, an image based on the image data acquired by the other imaging unit, and changes the positions of the first and second display regions according to the determination result of the position of the capsule endoscope.

According to another aspect of the present invention, a method of operating an image display that displays an image corresponding to image data obtained by a capsule endoscope which includes a first imaging unit capturing an image in a first direction and a second imaging unit capturing an image in a second direction different from the first direction, is introduced into a subject, and captures an in-vivo image of the subject includes: determining a moving direction of the capsule endoscope during imaging, specifying one of the first and second imaging units which faces the moving direction of the capsule endoscope during imaging, and determining the posture of the capsule endoscope; generating a display screen which includes a first display region in which an image in the moving direction of the capsule endoscope is arranged and a second display region in which an image in a direction opposite to the moving direction of the capsule endoscope is arranged, and on which an image based on the image data acquired by the imaging unit which is specified to face the moving direction is arranged in the first display region, an image based on the image data acquired by the other imaging unit is arranged in the second display region, and the positions of the first and second display regions are changed according to the determination result of the position of the capsule endoscope; and displaying the generated display screen.

According to still another aspect of the present invention, a computer-readable recording medium having stored thereon an executable image display program that causes an image display to display an image corresponding to image data obtained by a capsule endoscope which includes a first imaging unit capturing an image in a first direction and a second imaging unit capturing an image in a second direction different from the first direction, is introduced into a subject, and captures an in-vivo image of the subject and causes a processor to perform: determining a moving direction of the capsule endoscope during imaging, specifying one of the first and second imaging units which faces the moving direction of the capsule endoscope during imaging, and determining the posture of the capsule endoscope; generating a display screen which includes a first display region in which an image in the moving direction of the capsule endoscope is arranged and a second display region in which an image in a direction opposite to the moving direction of the capsule endoscope is arranged, and on which an image based on the image data acquired by the imaging unit which is specified to face the moving direction is arranged in the first display region, an image based on the image data acquired by the other imaging unit is arranged in the second display region, and the positions of the first and second display regions are changed according to the determination result of the position of the capsule endoscope; and displaying the generated display screen.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
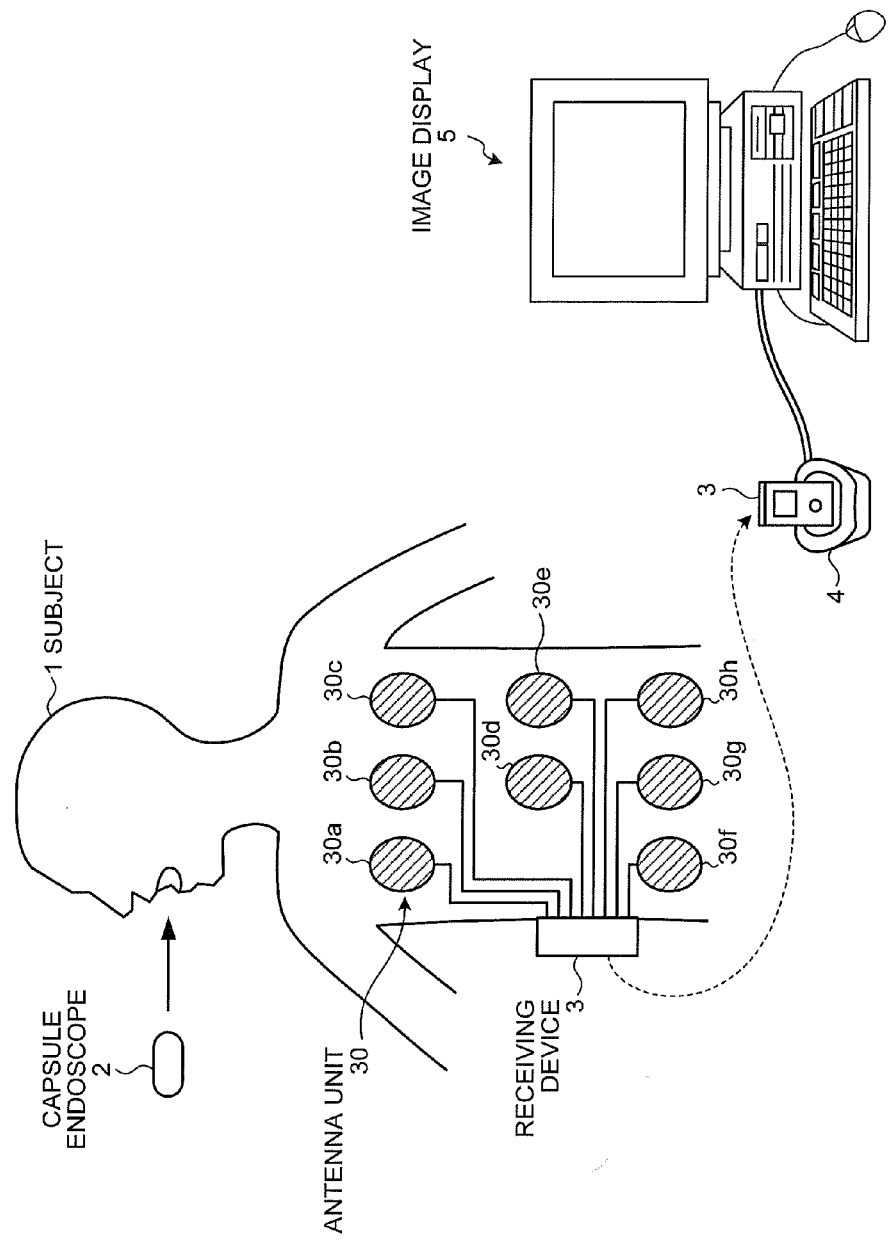
FIG. 1 is a diagram illustrating an example of the schematic structure of a capsule endoscope system according to a first embodiment of the invention.

Hereinafter, a capsule endoscope system, a method of operating an image display, and a computer-readable recording medium according to embodiments of the invention will be described with reference to the accompanying drawings. In the following description, for example, an image display which displays an image (hereinafter, referred to as an in-vivo image) acquired by a capsule endoscope that is introduced into the body of a subject and captures the image of the inside of the lumen (alimentary canal) is given as an example. However, the invention is not limited by the embodiments. In addition, in the following description, the drawings schematically illustrate the shape, size, and positional relationship of components such that the content of the invention can be understood. Therefore, the invention is not limited only to the shape, size, and positional relationship of the components illustrated in the drawings.

First Embodiment

FIG. 1 is a diagram illustrating an example of the schematic structure of a capsule endoscope system according to a first embodiment of the invention. The capsule endoscope system illustrated in FIG. 1 includes a capsule endoscope 2 that is introduced into the body of a subject 1, captures an in-vivo image, and wirelessly transmits image data corresponding to the in-vivo image, a receiving device 3 that receives the image data wirelessly transmitted from the capsule endoscope 2 through an antenna unit 30 including receiving antennas 30a to 30h, and an image display 5 that displays the in-vivo image based on the image data which is transmitted from the receiving device 3 through a cradle 4. Each of the receiving antennas 30a to 30h is implemented by, for example, a loop antenna and is arranged at a predetermined position (for example, a position corresponding to each organ in the subject 1 which is a passage of the capsule endoscope 2) on the outer surface of the body of the subject 1.

Figure 2:
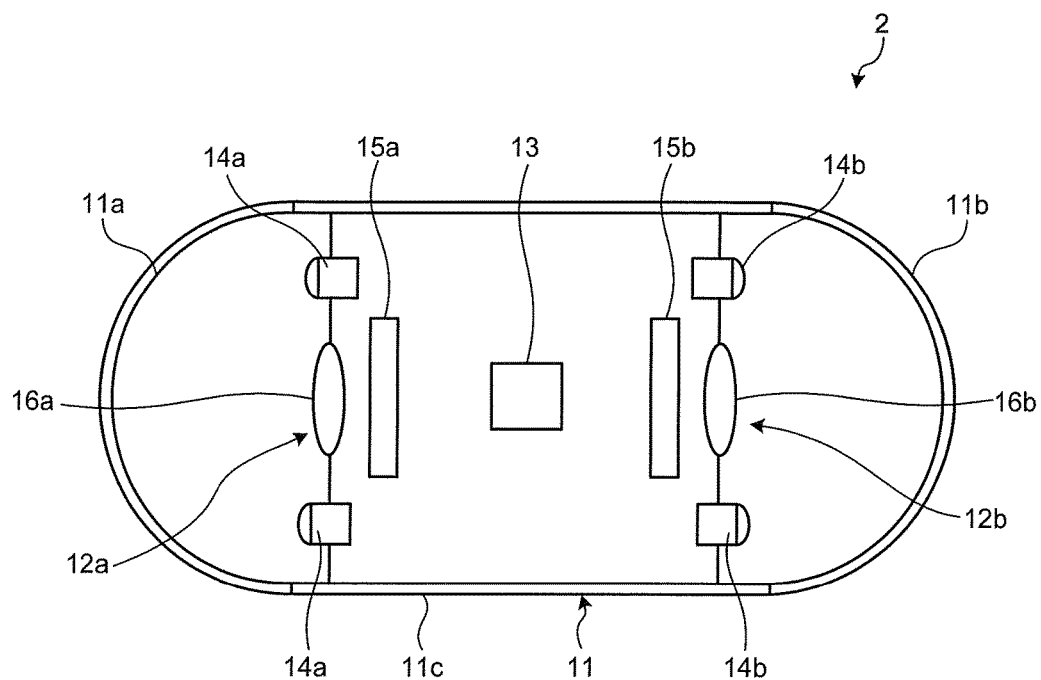
FIG. 2 is a longitudinal cross-sectional view illustrating the schematic structure of a capsule endoscope illustrated in FIG. 1.
Figure 3:
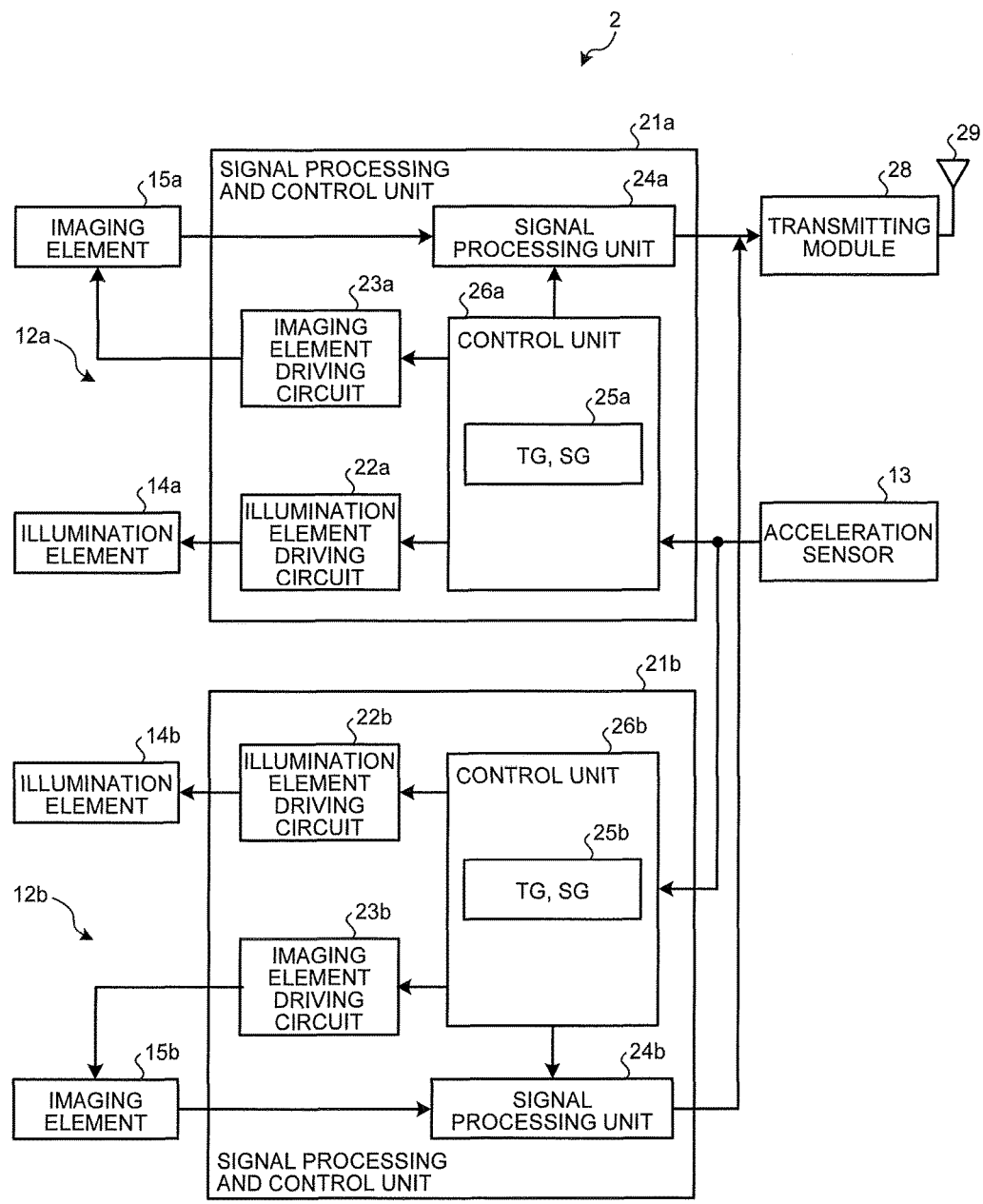
FIG. 3 is a block diagram illustrating the schematic structure of the capsule endoscope illustrated in FIG. 2.

FIG. 2 is a longitudinal cross-section view illustrating the schematic structure of the capsule endoscope 2. FIG. 3 is a block diagram illustrating the schematic structure of the capsule endoscope 2. The capsule endoscope 2 is a pantoscopic capsule endoscope including a plurality of imaging units. In the first embodiment, the capsule endoscope 2 includes two imaging units.

As illustrated in FIGS. 2 and 3, the capsule endoscope 2 includes a capsule-shaped casing 11 that can be introduced into the lumens of the subject 1, two imaging units 12a and 12b that are accommodated in the capsule-shaped casing 11 and capture images in the front-rear direction, an acceleration sensor 13 serving as a unit for detecting the posture of the capsule endoscope 2, signal processing and control units 21a and 21b corresponding to the imaging units 12a and 12b, and a transmission module 28 and a transmitting antenna 29 that transmit image data generated by the signal processing and control units 21a and 21b. In addition, the capsule endoscope 2 includes a battery, circuit components and the like (not illustrated).

The capsule-shaped casing 11 has a size that is swallowable from the mouth of the subject 1 and includes end covers 11a and 11b that have a substantially hemispherical shape and are transparent or translucent and a middle cover 11c that has a cylindrical shape and is made of a colored material which does not transmit visible light. The covers are elastically coupled to each other to form an outer casing whose inside is liquid-tightly sealed.

The imaging unit 12a includes a plurality of illumination elements 14a, such as LEDs that emit illumination light for illuminating the inside of the subject 1 (lumen) through the end cover 11a, an imaging element 15a, such as a CCD or a CMOS that receives the reflected light of the illumination light and captures the in-vivo image of the subject, and an imaging lens 16a that forms the in-vivo image of the subject on the imaging element 15a, and captures an image in the end direction of the end cover 11a.

The imaging unit 12b includes a plurality of illumination elements 14b, such as LEDs that emit illumination light for illuminating the inside of the subject through the end cover 11b, an imaging element 15b, such as a CCD or a CMOS that receives the reflected light of the illumination light and captures the in-vivo image of the subject, and an imaging lens 16b that forms the in-vivo image of the subject on the imaging element 15b, and captures an image in the end direction of the end cover 11b.

The acceleration sensor 13 is provided, for example, in the vicinity of the center of the capsule-shaped casing 11, detects acceleration in a triaxial direction which is applied to the capsule-shaped casing 11, and outputs the detected signal. In addition, the positional relationship between the acceleration sensor 13 and the imaging units 12a and 12b is set and stored in advance. In this way, it is possible to determine the posture of the capsule endoscope 2 on the basis of the detected signal from the acceleration sensor 13 and specify the positional relationship (for example, the upper side/the lower side and the front side/the rear side) of the imaging units 12a and 12b.

The signal processing and control unit 21a is provided so as to correspond to the imaging unit 12a and includes an illumination element driving circuit 22a that drives the illumination element 14a, an imaging element driving circuit 23a that drives the imaging element 15a, a signal processing unit 24a that performs predetermined signal processing for the signal output from the imaging element 15a, and a control unit 26a that controls the operations of the units. The signal processing unit 24a performs predetermined signal processing, such as a correlated double sampling process, an amplification process, an A/D conversion process, and a multiplexing process, for the signal output from the imaging element 15a to generate image data corresponding to an imaging region in the subject. The control unit 26a includes a timing generator and synchronous generator (TG, SG) 25a that generates various kinds of timing signals or synchronous signals and controls, for example, the operation of the driving circuits 22a and 23a and the signal processing unit 24a or the operation timing thereof, based on the timing signals or the synchronous signals generated by the timing generator and synchronous generator 25a. In addition, the control unit 26a performs predetermined signal processing (for example, the A/D conversion process) for the detected signal output from the acceleration sensor 13 and stores the processed signal as information about the posture of the capsule endoscope 2 so as to be associated with image data corresponding to when the detected signal is detected.

The signal processing and control unit 21b is provided so as to correspond to the imaging unit 12b and includes an illumination element driving circuit 22b that drives the illumination element 14b, an imaging element driving circuit 23b that drives the imaging element 15b, a signal processing unit 24b that performs predetermined signal processing for the signal output from the imaging element 15b, and a control unit 26b that controls the operation of the units based on the timing signals or the synchronous signals generated by a timing generator and synchronous generator (TG, SG) 25b. The operation of each unit is the same as that in the signal processing and control unit 21a.

Figure 4:
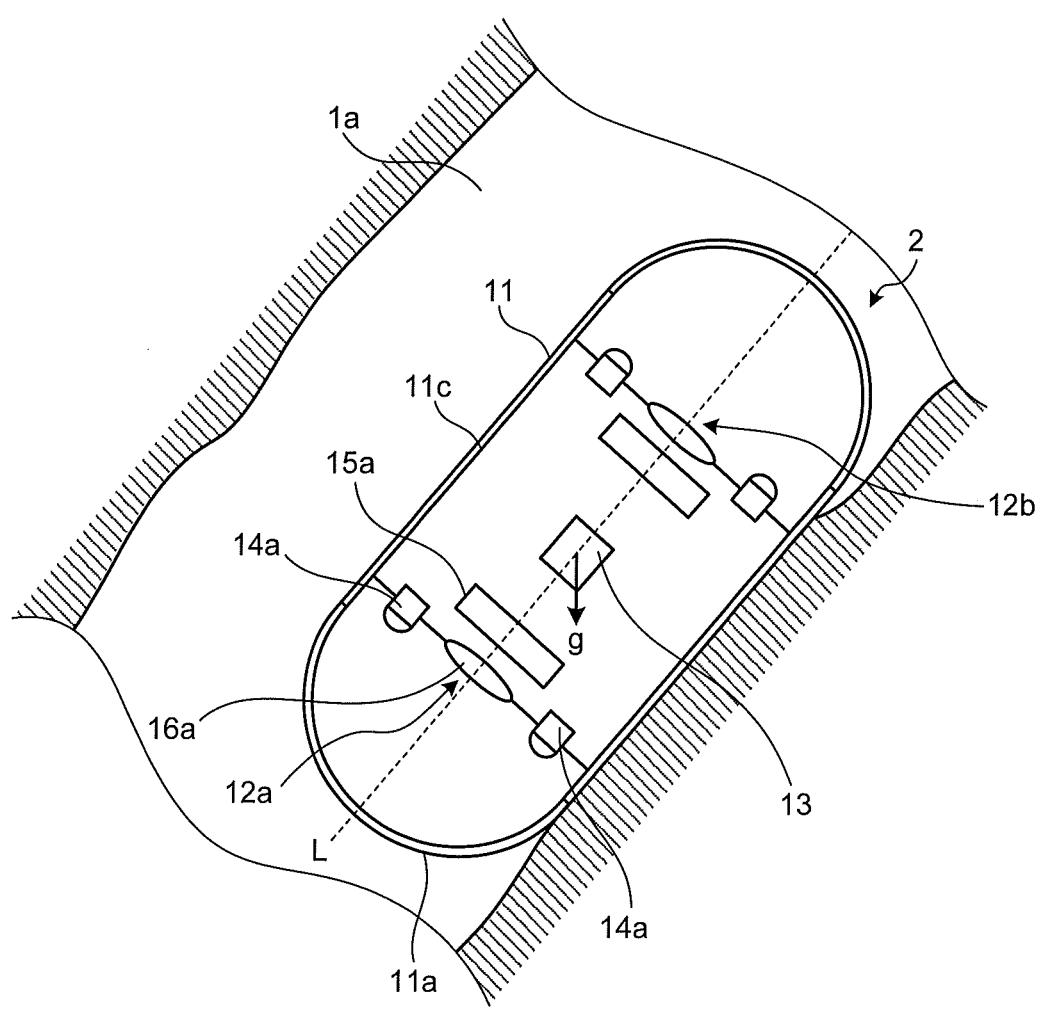
FIG. 4 is a schematic diagram illustrating an aspect of the movement of the capsule endoscope in a subject.

After the capsule endoscope 2 is swallowed from the mouth of the subject 1, it is moved into a lumen 1a of the subject 1 by, for example, the peristaltic motion of the organs, as illustrated in FIG. 4. While the capsule endoscope 2 is being moved, the imaging units 12a and 12b sequentially capture the images of parts of the body (for example, the esophagus, the stomach, the small intestine, and the large intestine) at a predetermined time interval (for example, an interval of 0.5 seconds) and the acceleration sensor 13 detects acceleration along the axis L of the capsule endoscope 2 and two axes perpendicular to the axis L. In FIG. 4, an arrow g indicates the direction of gravity acceleration. The obtained image data and related information (for example, information about the posture) are sequentially transmitted to the receiving device 3.

Figure 5:
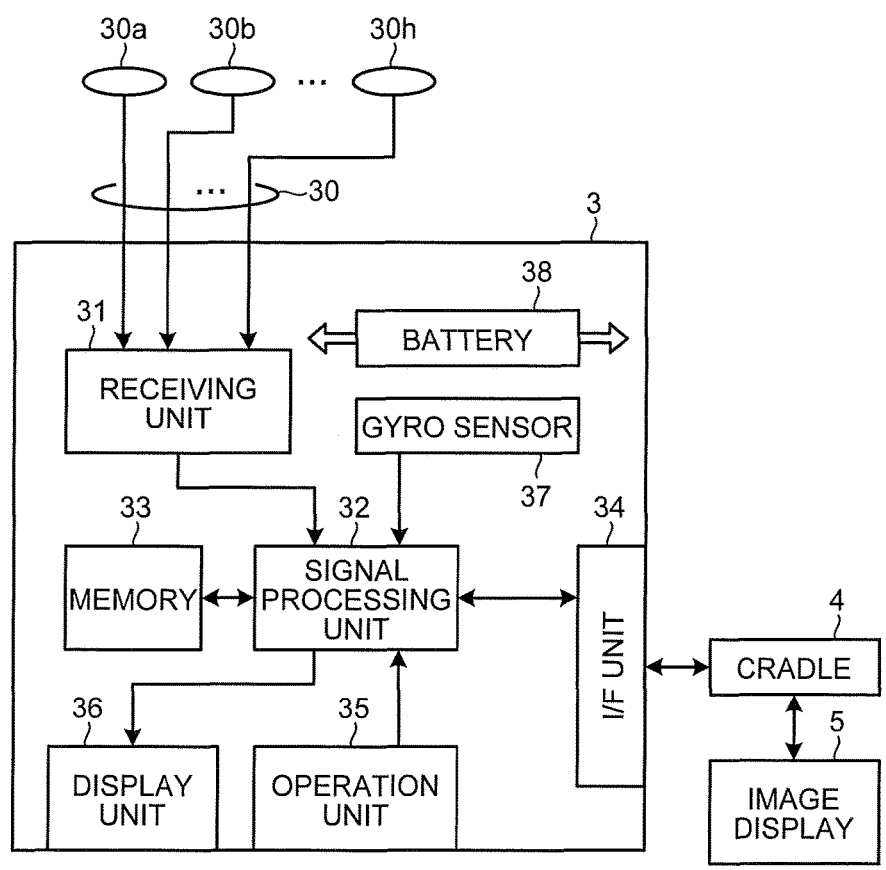
FIG. 5 is a block diagram illustrating the schematic structure of a receiving device illustrated in FIG. 1.

FIG. 5 is a block diagram illustrating the structure of the receiving device 3. As illustrated in FIG. 5, the receiving device 3 includes a receiving unit 31 that sequentially receives the image data and the related information wirelessly transmitted from the capsule endoscope 2 through the antenna unit 30, a signal processing unit 32 that controls the operation of each unit in the receiving device 3 and performs predetermined image processing for the received image data, a memory 33 that stores the processed image data and related information, an interface (I/F) unit 34 that transmits the image data and the related information stored in the memory 33 to the image display 5 through the cradle 4, an operation unit 35 that is used by the user to input various operation instructions or settings to the receiving device 3, a display unit 36 that notifies or displays various kinds of information to the user, a gyro sensor 37 serving as a posture detecting unit of the receiving device 3, and a battery 38 that supplies power to each of the above-mentioned units.

The gyro sensor 37 detects the angular velocity of the receiving device 3 and is provided in order to determine the posture (for example, a standing posture or a recumbent posture) of the receiving device 3, that is, the posture of the subject 1 with the receiving device 3. The signal processing unit 32 performs predetermined signal processing (for example, A/D conversion) for the signal detected by the gyro sensor 37 and the processed detected signal is stored as information about the posture of the subject 1 so as to be associated with the image data corresponding to when the detection signal is detected (for example, received at that time).

After the capture of the images by the capsule endoscope 2 ends, the receiving device 3 is detached from the subject 1 and is then set to the cradle 4 which is connected to, for example, a USB port of the image display 5. Then, the receiving device 3 is connected to the image display 5 and the image data and the related information stored in the memory 33 are transmitted to the image display 5.

The transmission of, for example, the image data to the image display 5 is not limited to the method of transmitting the image data through the cradle 4. For example, when the image data stored in a server is processed, it may be acquired through a communicate device connected to the server. When image data stored in a portable recording medium, such as a CD-R or a DVD-R, is processed, for example, a reading device provided in the image display 5 may read the image data from the recording medium. Alternatively, a medical observation device may be connected to the image display 5 and image data may be directly acquired from the medical observation device.

Figure 6:
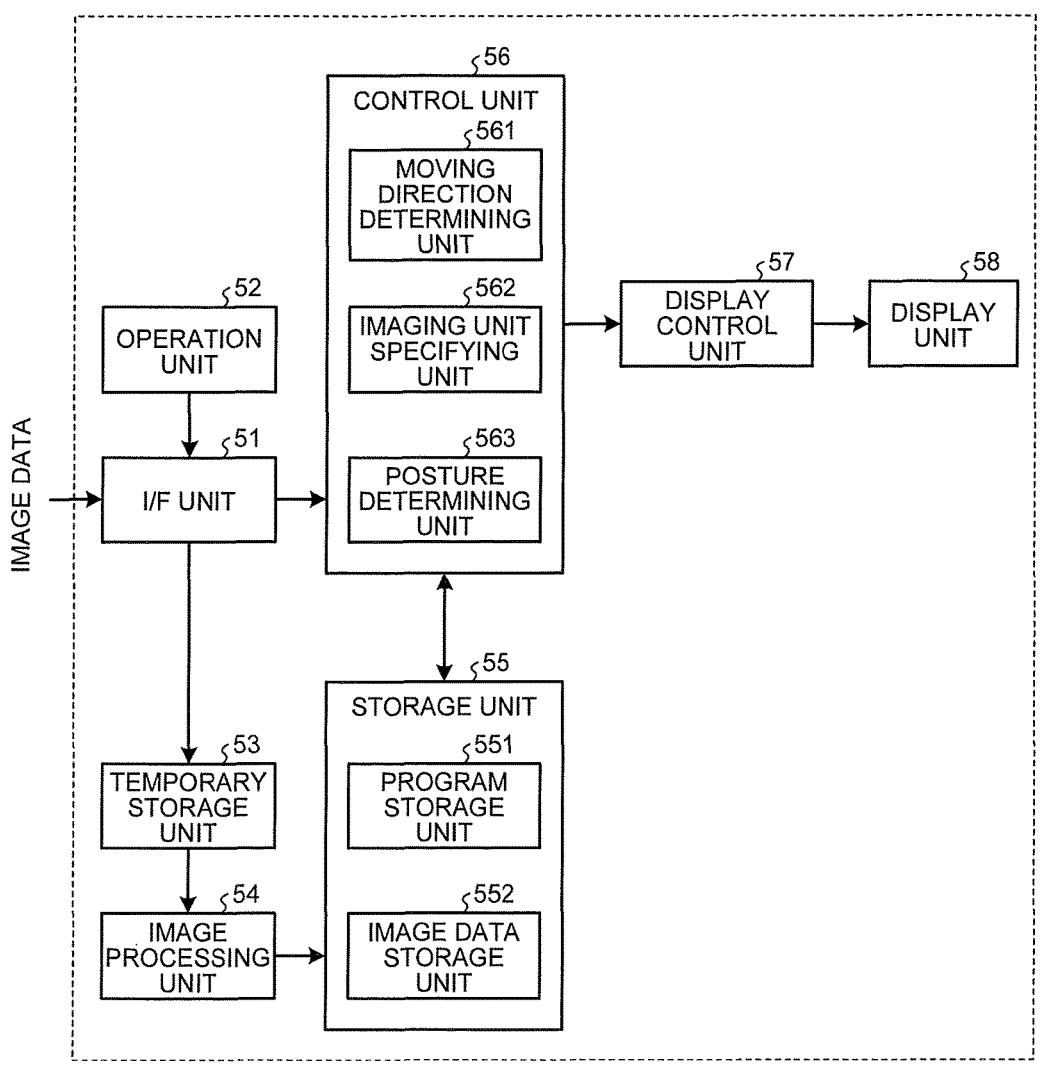
FIG. 6 is a block diagram illustrating the schematic structure of an image display illustrated in FIG. 1.

FIG. 6 is a block diagram illustrating the structure of the image display 5. The image display 5 is implemented by, for example, a workstation or a personal computer including a display screen such as a monitor.

As illustrated in FIG. 6, the image display 5 includes an interface (I/F) unit 51 that receives input image data corresponding to the in-vivo image, an operation unit 52 that is used by the user to input various kinds of information or commands, a temporary storage unit 53 that temporarily stores the image data input from the interface unit 51, an image processing unit 54 that performs image processing for the image data stored in the temporary storage unit 53, a storage unit 55 that stores the processed image data, a control unit 56 that controls the operation of each unit in the image display 5 and performs various determination processes on the basis of information related to the image data, a display control unit 57 that generates an observation screen on which in-vivo images are arranged in a predetermined format, and a display unit 58 that displays the observation screen under the control of the display control unit 57.

The interface unit 51 includes a connection port (for example, a USB port) to an external device (for example, a reading device which reads image data from a portable recording medium) and receives the input of signals indicating the image data which is input through the connection port and information related to the image data.

The operation unit 52 is implemented by, for example, an input device, such as a keyboard, a mouse, a touch panel, or various kinds of switches. The operation unit 52 receives the input of an operation signal corresponding to the operation of the user and outputs the operation signal to the control unit 56 through the interface unit 51.

The temporary storage unit 53 is implemented by a volatile memory, such as a DRAM or an SRAM, and temporarily stores the image data which is input through the interface unit 51 and information related to the image data. Alternatively, instead of the temporary storage unit 53, a recording medium, such as an HDD, an MO, a CD-R, or a DVD-R, and a driving device that drives the recording medium may be provided, and the image data input from the interface unit 51 may be temporarily stored in the recording medium.

The image processing unit 54 performs image processing, such as white balance processing, demosaicing, color conversion, density conversion (for example, gamma conversion), smoothing (for example, noise removal), or sharpening (for example, edge emphasis), for the image data stored in the temporary storage unit 53 to generate display image data corresponding to a series of images.

The storage unit 55 is implemented by a semiconductor memory, such as a flash memory, a RAM, or a ROM, or a recording medium, such as an HDD, an MO, a CD-R, or a DVD-R, and a driving device that drives the recording medium. The storage unit 55 includes a program storage unit 551 that stores a program for operating the image display 5 and for causing the image display 5 to perform various functions and data which is used during the execution of the program and an image data storage unit 552 that stores the image data and the related information. Specifically, the program storage unit 551 stores an image display program for displaying an image corresponding to the image data which is acquired by the capsule endoscope 2 on the image display 5 in a predetermined format.

The control unit 56 is implemented by hardware, such as a CPU, reads the program stored in the program storage unit 551, transmits, for example, instructions or data to each unit of the image display 5 according to the image data and the related information, or various operation signals input through the interface unit 51, and controls the overall operation of the image display 5. In addition, the control unit 56 includes a moving direction determining unit 561 that determines the direction in which the capsule endoscope 2 moves at the time when each in-vivo image is captured, an imaging unit specifying unit 562 that specifies an imaging unit which faces the moving direction and an imaging unit which faces a direction opposite to the moving direction of the imaging units 12a and 12b in the capsule endoscope 2 based on the determination result of the moving direction determining unit 561, and a posture determining unit 563 that determines the posture of the capsule endoscope 2 based on information about the posture of the capsule endoscope 2 which is associated with the image data. The posture of the capsule endoscope 2 means, for example, the positional relationship between the imaging units 12a and 12b in the vertical direction or the depth direction with respect to a predetermined coordinate axis. Examples of the coordinate axis include two axes perpendicular to the moving direction of the capsule endoscope 2 and the gravity acceleration direction.

The display control unit 57 generates an observation screen on which two in-vivo images captured by the two imaging units 12a and 12b are arranged, using the image data stored in the image data storage unit 552, and displays the observation screen on the display unit 58.

The display unit 58 is implemented by a display device, such as a CRT display, a liquid crystal display, or an EL display. The display unit 58 displays the observation screen or other screens in a predetermined format under the control of the display control unit 57.

Figure 7:
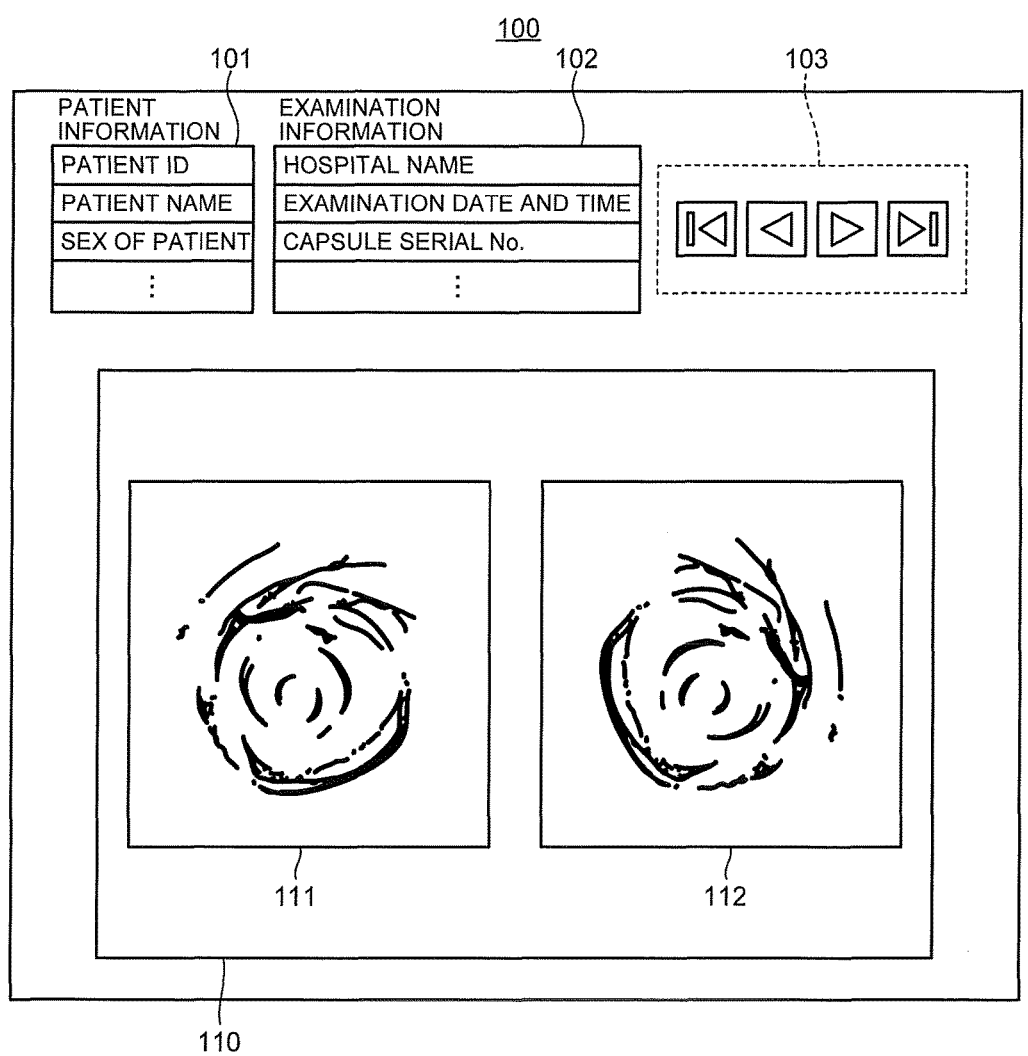
FIG. 7 is a schematic diagram illustrating an observation screen displayed on a display unit illustrated in FIG. 6.

FIG. 7 is a diagram schematically illustrating an example of the observation screen which is generated by the display control unit 57 and is then displayed on the display unit 58. As illustrated in FIG. 7, an observation screen 100 includes a patient information display region 101 in which patient information for identifying the subject 1, which is a patient, is displayed, an examination information display region 102 in which examination information for identifying examination for the subject 1 is displayed, a reproducing operation button group 103 that receives the input of an operation for reproducing the in-vivo image, and an image display region 110 in which a series of in-vivo images is reproduced and displayed. The patient information includes, for example, a patient ID, a patient name, and the sex of the patient. In addition, the examination information includes, for example, the name of the hospital where the patient is examined, examination date and time, and the serial number of the capsule endoscope 2 used.

The image display region 110 includes two display regions 111 and 112 in which the in-vivo images captured by the imaging units 12a and 12b are arranged. Of the two display regions 111 and 112, the display region 111 is set as a region in which the in-vivo image facing the moving direction is arranged and the display region 112 is set as a region in which the in-vivo image facing the direction opposite to the moving direction of the capsule endoscope 2 is arranged. In the first embodiment, the position of the display region 111 is fixed to the left side of the image display region 110 and the position of the display region 112 is fixed to the right side of the image display region 110.

Figure 8:
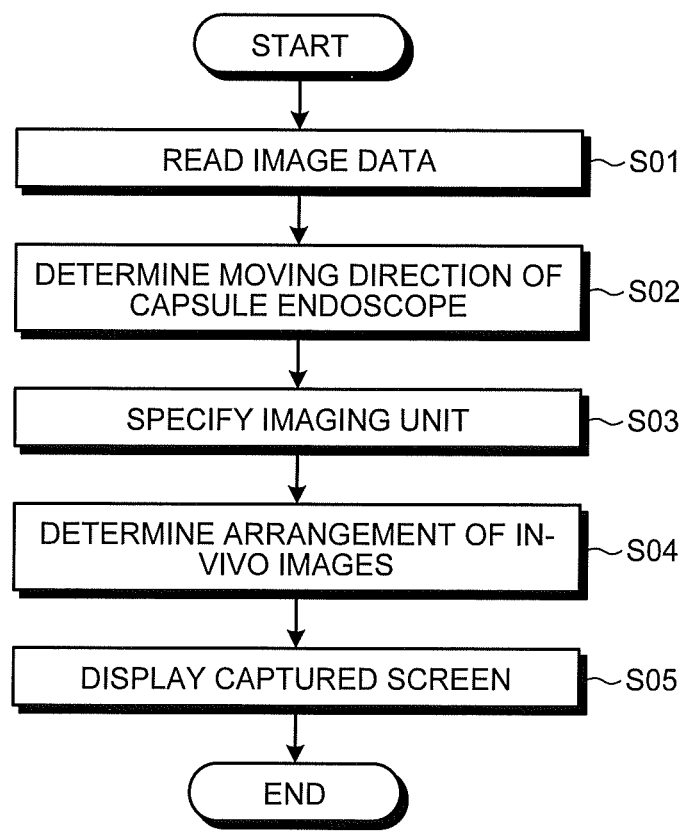
FIG. 8 is a flowchart illustrating the operation of the image display in an in-vivo image display process.

Next, an in-vivo image display process according to the first embodiment will be described. FIG. 8 is a flowchart illustrating the operation of the image display 5 in the in-vivo image display process.

First, in Step S01, the control unit 56 reads the image data of the in-vivo image from the image data storage unit 552.

Then, in Step S02, the moving direction determining unit 561 determines the moving direction of the capsule endoscope 2 at the time when the in-vivo image, which is a display target, is captured. In the first embodiment, the moving direction is a direction from the mouth to the anus of the subject 1 along the length direction of the lumen. Various known methods may be used as a method of determining the moving direction. Next, for example, a method of determining the moving direction on the basis of the amount of movement of the in-vivo image will be described.

First, the moving direction determining unit 561 estimates the amount of movement of the capsule endoscope 2 between the capture time t(i) of an i-th (i=1, 2, . . . ) in-vivo image $G_i$, which is a display target, and the capture time t(i+Δ) of the next in-vivo image $G_{i+\Delta}$ on the basis of the in-vivo images $G_i$ and $G_{i+\Delta}$. The interval Δ (Δ is an integer) between the in-vivo images is set to a relatively large value. The reason is as follows. Since the capsule endoscope 2 moves step by step while reciprocating due to the influence of, for example, the peristaltic motion of the subject 1, the influence of the local reciprocation is excluded and the global moving direction (that is, the direction from the mouth to the anus) of the capsule endoscope 2 is detected. Therefore, the time interval between the capture time t(i) and the capture time t(i+Δ) may be set to a relatively large value. For example, the average period of the peristaltic motion of the subject 1 may be acquired in advance and the time interval may be set based on the average period. Specifically, when the average number of peristaltic motions of the subject 1 per minute is 6, the time interval is set to, about, 10 seconds which are the average period of the peristaltic motion.

Figure 9A:
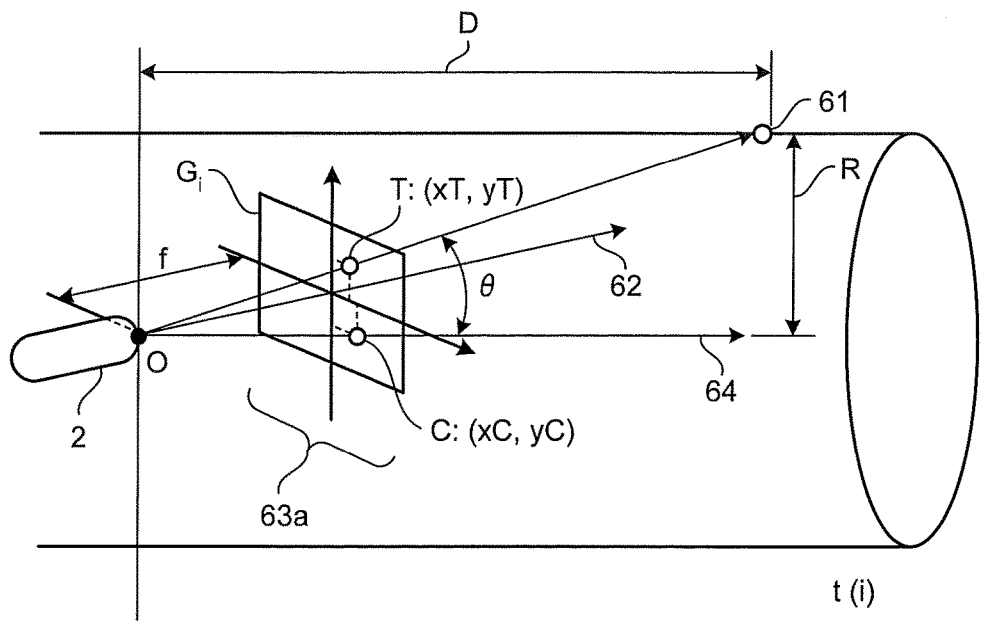
FIGS. 9A and 9B are diagrams illustrating a method of estimating the amount of movement of the capsule endoscope.
Figure 9B:
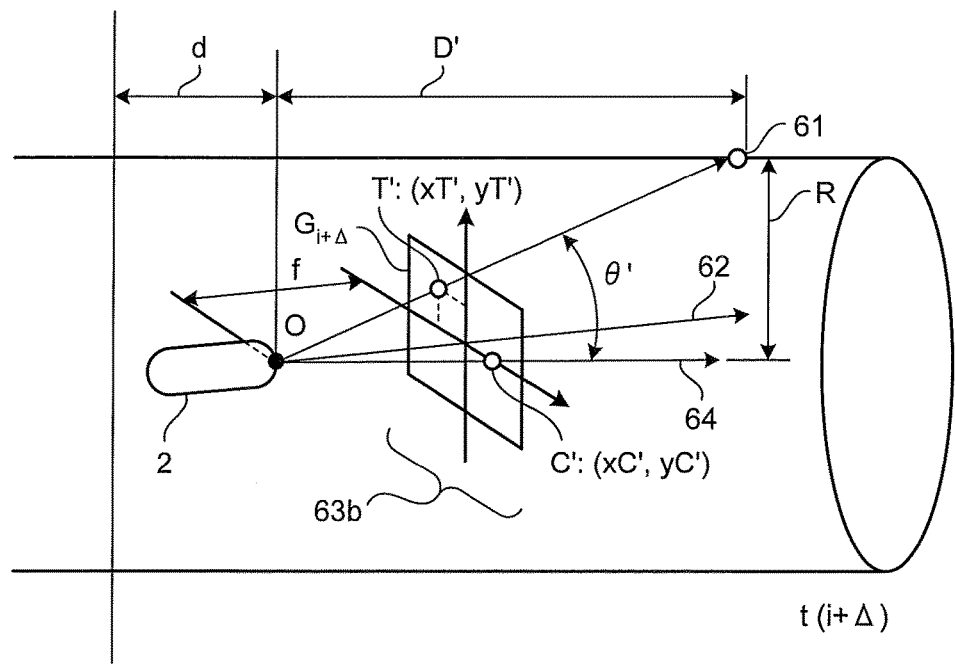

FIGS. 9A and 9B are diagrams illustrating the method of estimating the amount of movement of the capsule endoscope 2. FIG. 9A illustrates the imaging condition model of the capsule endoscope 2 which captures the in-vivo image $G_i$ at the capture time t(i) and FIG. 9B illustrates the imaging condition model of the capsule endoscope 2 which captures the in-vivo image $G_{i+\Delta}$ at the capture time t(i+Δ). The in-vivo images $G_i$ and $G_{i+\Delta}$ include a corresponding feature structure 61. The feature structure 61 is a structure which characterizes a local part on the mucous membrane of the lumen and specifically corresponds to, for example, the blood vessel which is seen through the wrinkle or surface of the mucous membrane of the lumen.

In FIGS. 9A and 9B, letter D indicates a feature structure distance obtained by projecting a distance from the capsule endoscope 2 to the feature structure 61 on the mucous membrane of the lumen at the capture time t(i) onto the inner wall of the lumen and letter D' indicates a feature structure distance obtained by projecting a distance from the capsule endoscope 2 to the feature structure 61 on the mucous membrane of the lumen at the capture time t(i+Δ). Letter O indicates an optical center corresponding to the principal point of an optical system, such as a lens of the capsule endoscope 2. For example, the average radius of the lumen is used as the radius R of the lumen.

In addition, image coordinates 63a illustrated in FIG. 9A are the coordinates of the in-vivo image $G_i$ projected onto the imaging element of the capsule endoscope 2. The image coordinates 63a are in a coordinate system which has a point intersecting an optical axis 62 of the capsule endoscope 2 as the origin and the gap from the optical center O of the capsule endoscope 2 to the imaging element is a distance f. It is assumed that the coordinates of the center of a structure region in which the feature structure 61 of the in-vivo image obtained by the imaging situation model is seen are structure region center coordinates T (xT, yT) and the coordinates of the center of gravity of a deep part of the lumen in the in-vivo image are lumen deep part gravity center coordinates C (xC, yC). In addition, it is assumed that an angle θ is the angle formed between a vector OC from the optical center O in the direction 64 of the center of gravity of the deep part of the lumen and a vector OT from the optical center O to the feature structure 61 at the capture time t(i).

Similarly, image coordinates 63b illustrated in FIG. 9B are the coordinates of the in-vivo image $G_{i+\Delta}$. The image coordinates 63b are in the coordinate system which has the point intersecting the optical axis 62 of the capsule endoscope 2 as the origin and the gap from the optical center O of the capsule endoscope 2 to the imaging element is the distance f. It is assumed that the coordinates of the center of a corresponding region in which the feature structure 61 of the in-vivo image obtained by the imaging situation model is seen are corresponding region center coordinates T' (xT', yT') and the coordinates of the center of gravity of the deep part of the lumen in the in-vivo image are lumen deep part gravity center coordinates C' (xC', yC'). In addition, it is assumed that an angle θ' is the angle formed between a vector OC' from the optical center O in the direction 64 of the center of gravity of the deep part of the lumen and a vector OT' from the optical center O to the feature structure 61 at the capture time t(i+Δ).

In the imaging condition model illustrated in FIG. 9B, a variation in the imaging position (the position of the capsule endoscope 2) and a variation in the imaging direction occur, as compared to the imaging situation model illustrated in FIG. 9A.

The following Expression 1 is obtained from the feature structure distance D, the structure region center coordinates T, the lumen deep part gravity center coordinates C, the distance f, and the lumen radius R in the imaging situation model illustrated in FIG. 9A:

$$\frac{R}{D} = \tan\theta = \frac{\sqrt{1-\cos^2\theta}}{\cos\theta} \qquad (1)$$

-continued $$\cos\theta = \frac{\overrightarrow{OT} \cdot \overrightarrow{OC}}{|\overrightarrow{OT}| \times |\overrightarrow{OC}|}$$

$$= \frac{(xT \times \delta) \times (xC \times \delta) + (yT \times \delta) \times (yC \times \delta) + f^2}{\sqrt{(xT \times \delta)^2 + (yT \times \delta)^2 + f^2} \times \sqrt{(xC \times \delta)^2 + (yC \times \delta)^2 + f^2}}$$

(where, δ indicates the pitch between the imaging elements of the capsule endoscope 2).

The distance f and the value of each camera parameter of the pitch δ between the imaging elements are acquired in advance.

Similarly, the following Expression 2 is obtained from the feature structure distance D', the corresponding region center coordinates T', the lumen deep part gravity center coordinates C', the distance f, and the lumen radius R in the imaging situation model illustrated in FIG. 9B:

$$\frac{R}{D'} = \frac{\sqrt{1 - \cos^2\theta'}}{\cos\theta'} \quad (2)$$

$$\cos\theta' = \frac{\overrightarrow{OT'} \cdot \overrightarrow{OC'}}{|\overrightarrow{OT'}| \times |\overrightarrow{OC'}|}$$

$$= \frac{(xT' \times \delta) \times (xC' \times \delta) + (yT' \times \delta) \times (yC' \times \delta) + f^2}{\sqrt{(xT' \times \delta)^2 + (yT' \times \delta)^2 + f^2} \times \sqrt{(xC' \times \delta)^2 + (yC' \times \delta)^2 + f^2}}$$

The following Expression 3 is obtained from Expression 1 and Expression 2:

$$\frac{R}{D} - \frac{R}{D'} = \frac{\sqrt{1 - \cos^2\theta}}{\cos\theta} - \frac{\sqrt{1 - \cos^2\theta'}}{\cos\theta'} \quad (3)$$

Expression 3 is changed to obtain the following Expression 4:

$$D - D' = \left(\frac{\cos\theta}{\sqrt{1 - \cos^2\theta}} - \frac{\cos\theta'}{\sqrt{1 - \cos^2\theta'}}\right) \times R \quad (4)$$

A value D-D' which is given by Expression 4 is the difference between the feature structure distances obtained by projecting the distances from the capsule endoscope 2 to the feature structure 61 on the mucous membrane of the lumen at the capture times t(i) and t(i+Δ) onto the inner wall of the lumen and corresponds to the amount of movement d of the capsule endoscope 2 from the capture time t(i) to the capture time (i+Δ) illustrated in FIG. 9B.

The moving direction determining unit 561 calculates the value D-D' for each feature structure included in the in-vivo images and calculates the average value of the values D-D'. The average value is estimated as the amount of movement of the capsule endoscope 2 from the capture time t(i) to the capture time t(i+Δ). Hereinafter, the average value of the values D-D' is referred to as the amount of movement E.

The moving direction determining unit 561 calculates the amount of movement E for the in-vivo images captured by the imaging units 12a and 12b. Then, the moving direction determining unit 561 determines that the direction of the imaging unit with the positive amount of movement E is the moving direction.

The details of the method of estimating the amount of movement which is used as an example of the moving direction determining method in Step S02 are disclosed in Japanese Patent Application Laid-open No. 2008-301877.

Then, in Step S03, the imaging unit specifying unit 562 specifies the imaging unit which faces the moving direction at the imaging time based on the determination result of the moving direction determining unit 561. Here, the imaging unit facing the moving direction includes the imaging unit satisfying cos α>0 (where α is the angle formed between the moving direction of the capsule endoscope 2 and the optical axis when the emission direction of illumination light is a positive direction).

As described above, when the amount of movement E is used to determine the moving direction of the capsule endoscope 2, the process of determining the moving direction and the process of specifying the imaging unit facing the moving direction may be performed at the same time.

In Step S04, the display control unit 57 determines the arrangement of the in-vivo images captured by the imaging units 12a and 12b in the image display region 110. That is, the in-vivo image captured by the imaging unit which is specified to face the moving direction is arranged in the left (moving direction side) display region 111 and the in-vivo image captured by the imaging unit which is specified to face the direction opposite to the moving direction is arranged in the right (the side opposite to the moving direction) display region 112. In this way, the observation screen including the in-vivo images captured by the two imaging units 12a and 12b is displayed on the display unit 58 (Step S05).

Next, the detailed arrangement of the in-vivo images in the image display region 110 will be described with reference to schematic diagrams.

Figure 10A:
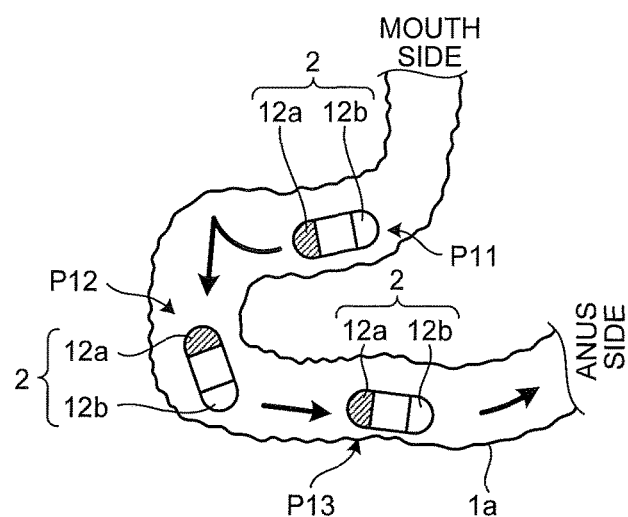
FIGS. 10A to 10D are diagrams illustrating an in-vivo image display method according to the first embodiment.
Figure 10B:
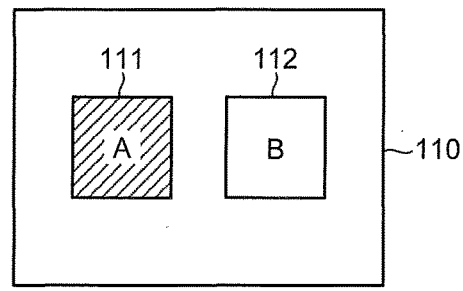
Figure 10C:
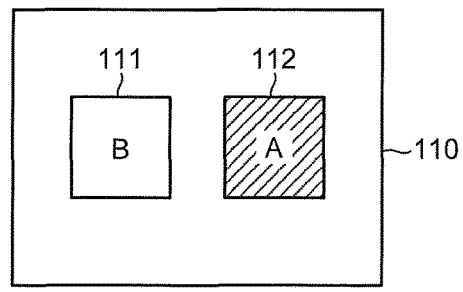
Figure 10D:
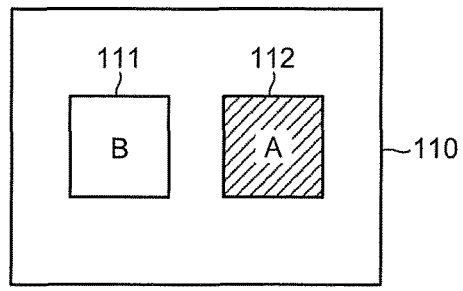

FIG. 10A is a schematic diagram illustrating the capsule endoscope 2 that moves in the lumen 1a of the subject 1. FIGS. 10B to 10D are schematic diagrams illustrating examples of the arrangement of the in-vivo images captured at positions P11, P12, and P13 illustrated in FIG. 10A. In the following description, the in-vivo image captured by the imaging unit 12a is referred to as an in-vivo image A and the in-vivo image captured by the imaging unit 12b is referred to as an in-vivo image B. In addition, in the following description, the imaging unit 12a is hatched for ease of recognition in the drawings. In FIGS. 10B to 10D, the in-vivo image A is hatched in order to clarify the correspondence with the imaging unit 12a.

As illustrated in FIG. 10A, the capsule endoscope 2 which has passed through the position P11 moves with the imaging unit 12a facing the anus. In this case, as illustrated in FIG. 10B, in the image display region 110 corresponding to the position P11, the in-vivo image A corresponding to the imaging unit 12a is arranged in the display region 111 which is disposed in the moving direction and the in-vivo image B corresponding to the imaging unit 12b is arranged in the display region 112 which is disposed in the direction opposite to the moving direction.

After passing through the position P11, the capsule endoscope 2 rotates back and forth and passes through the position P12 with the imaging unit 12b facing the anus. In this case, as illustrated in FIG. 10C, in the image display region 110 corresponding to the position P12, the in-vivo image B corresponding to the imaging unit 12b is arranged in the display region 111 which is disposed in the moving direction and the in-vivo image A corresponding to the imaging unit 12a is arranged in the display region 112 which is disposed in the direction opposite to the moving direction.

Then, the capsule endoscope 2 passes through the position P13 with the imaging unit 12b facing the anus. In this case, as illustrated in FIG. 10D, in the image display region 110 corresponding to the position P13, the in-vivo image B corresponding to the imaging unit 12b is arranged in the display region 111 which is disposed in the moving direction and the in-vivo image A corresponding to the imaging unit 12a is arranged in the display region 112 which is disposed in the direction opposite to the moving direction.

As described above, according to the first embodiment, on the screen including the first display region in which the image in the moving direction of the capsule endoscope 2 is arranged and the second display region in which the image in the direction opposite to the moving direction of the capsule endoscope 2 is arranged, the image based on the image data acquired by the imaging unit which is specified to face the moving direction during imaging is displayed in the first display region, and the image based on the image data acquired by the other imaging unit is arranged in the second display region. Therefore, the user can visually know the direction of the images captured by two imaging units or the moving direction of the capsule endoscope 2 with ease.

That is, the in-vivo image of a part which is close to the anus than the capsule endoscope 2 is constantly displayed in the display region 111 in the moving direction which is arranged on the left side of the screen and the in-vivo image of a part which is closer to the mouth than the capsule endoscope 2 is displayed in the display region 112 in the direction opposite to the moving direction which is arranged on the right side of the screen. Therefore, the user can visually know the direction (the anus side/the mouth side) of a part in the in-vivo image with ease. Therefore, even when observing a portion of the in-vivo image, the user can visually know the direction of each in-vivo image which is currently being displayed. In addition, since the user who is not an expert can intuitively know the moving direction of the capsule endoscope 2, it is possible to improve the efficiency of observation.

According to the first embodiment, since the in-vivo image including an anus-side part is constantly displayed on the same side, a rapid change in the background of one display region is reduced and it is possible to reduce the load (for example, an influence on the eye and fatigue) of the user during observation.

Second Embodiment

Next, a second embodiment of the invention will be described.

The structure of a capsule endoscope system according to the second embodiment is the same as that illustrated in FIGS. 1 to 6. the second embodiment differs from the first embodiment in the detailed operation of the moving direction determining unit 561.

The moving direction determining unit 561 detects, as the moving direction of the capsule endoscope 2, the moving direction of the capsule endoscope 2 at the moment when an in-vivo image is captured. In this case, it is possible to reflect the reciprocating motion of the capsule endoscope 2 due to the peristaltic motion in the display of the in-vivo image. The imaging unit specifying unit 562 specifies an imaging unit which faces the moving direction and an imaging unit which faces a direction opposite to the moving direction, based on the determination result of the moving direction determining unit 561. The display control unit 57 determines the arrangement of in-vivo images such that the in-vivo image captured by the imaging unit which is specified to face the moving direction is arranged in the display region 111 disposed in the moving direction and the in-vivo image captured by the imaging unit which is specified to face the direction opposite to the moving direction is arranged in the display region 112 disposed in the direction opposite to the moving direction.

In addition, similarly to the first embodiment, for example, the moving direction determining unit 561 may determine the moving direction based on the amount of movement E of the capsule endoscope 2. In this case, the interval Δ between the in-vivo images may be set to a small value (for example, Δ=1) and the amount of movement may be estimated. In this way, it is possible to calculate the local moving direction of the capsule endoscope 2. Alternatively, the moving direction determining unit 561 may detect the moving direction of the capsule endoscope 2 based on a detected signal which is detected by the acceleration sensor 13 of the capsule endoscope 2.

Next, the detailed arrangement of the in-vivo images according to the second embodiment will be described with reference to schematic diagrams.

Figure 11A:
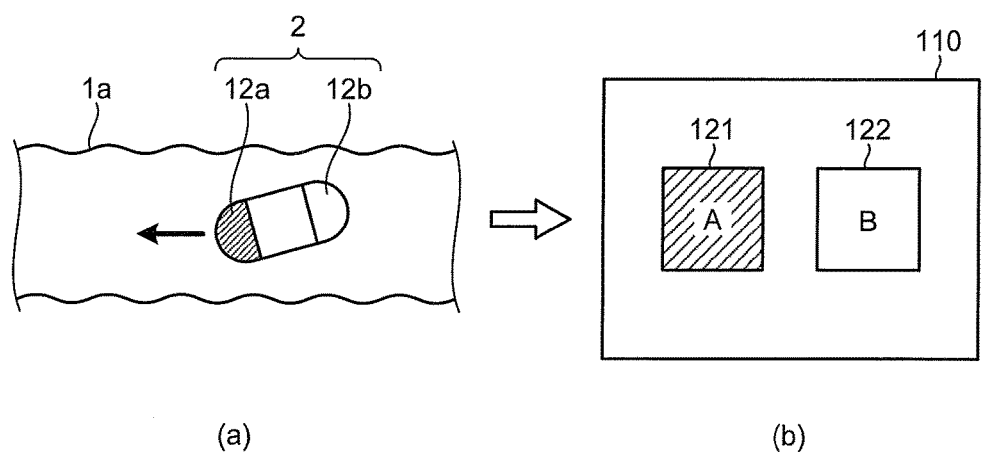
FIGS. 11A and 11B are schematic diagrams illustrating an in-vivo image display method according to a second embodiment.

(a) of FIG. 11A illustrates an aspect in which the capsule endoscope 2 moves to the left side in the lumen 1a with the imaging unit 12a facing to the left side of (a) of FIG. 11A. In this case, as illustrated in (b) of FIG. 11A, an in-vivo image A captured by the imaging unit 12a is arranged in a display region 121 which is disposed in the moving direction. On the other hand, an in-vivo image B captured by an imaging unit 12b is arranged in a display region 122 which is disposed in the direction opposite to the moving direction.

Figure 11B:
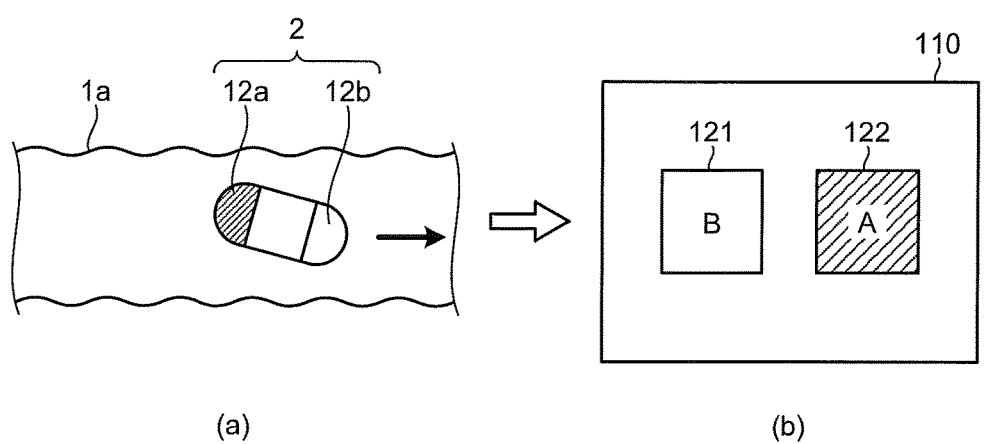

(a) of FIG. 11B illustrates an aspect in which the capsule endoscope 2 moves to the right side in the lumen 1a with the imaging unit 12b facing to the right side of (a) of FIG. 11B. In this case, as illustrated in (b) of FIG. 11B, the in-vivo image B captured by the imaging unit 12b is arranged in the display region 121 which is disposed in the moving direction. On the other hand, the in-vivo image A captured by an imaging unit 12a is arranged in the display region 122 which is disposed in the direction opposite to the moving direction.

As described above, according to the second embodiment, the user can visually know the direction of the in-vivo image with respect to the local moving direction of the capsule endoscope 2. In addition, the in-vivo image in the forward direction is constantly displayed in the display region 121 which is disposed in the moving direction and the in-vivo image in the backward direction is constantly displayed in the display region 122. Therefore, it is possible to reduce the burden (for example, the flickering of image) of the user who observes the screen. Even when the capsule endoscope 2 repeatedly moves forward and backward in the lumen 1a, the user does not misunderstand the same lesion as a different lesion. Therefore, it is possible to improve the efficiency of observation.

Third Embodiment

Next, a third embodiment of the invention will be described.

The structure of a capsule endoscope system according to the third embodiment is the same as that illustrated in FIGS. 1 to 6. the third embodiment differs from the first embodiment in that the determination result of the posture determining unit 563 for the posture of the capsule endoscope 2 is reflected in determining the arrangement of in-vivo images on an observation screen.

In this case, the posture determining unit 563 calculates the posture of the capsule endoscope 2 based on information about the posture of the capsule endoscope 2 which is associated with the image data of the in-vivo image and determines the positional relationship between the imaging units 12a and 12b. The imaging unit specifying unit 562 specifies an imaging unit which faces up and an imaging unit which faces down at the imaging time, based on the determination result of the posture determining unit 563. A display control unit 57 sets a display region (hereinafter, referred to as an upper display region) of an in-vivo image indicating the upper side (that is, the upper wall of the lumen 1a) of the capsule endoscope 2 and a display region (hereinafter, referred to as a lower display region) of an in-vivo image indicating the lower side (that is, the lower wall of the lumen 1a) of the capsule endoscope 2 to predetermined positions of the image display region 110. In addition, the display control unit 57 arranges the in-vivo image captured by the imaging unit which is determined to face up in the upper display region and arranges the in-vivo image captured by the imaging unit which is determined to face down in the lower display region, based on the specification result of the imaging unit specifying unit 562.

Figure 12A:
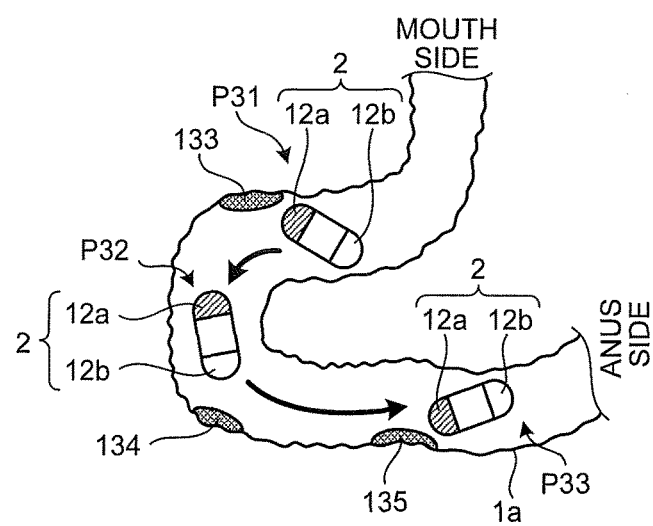
FIGS. 12A to 12D are schematic diagrams illustrating an in-vivo image display method according to a third embodiment.
Figure 12B:
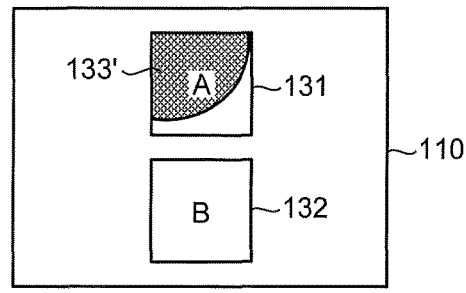

Next, the detailed arrangement of the in-vivo images in the third embodiment will be described with reference to schematic diagrams. As illustrated in FIG. 12A, the capsule endoscope 2 which has passed through a position P31 moves upward toward the imaging unit 12a. In this case, as illustrated in FIG. 12B, in the image display region 110 corresponding to the position P31, an in-vivo image A corresponding to the imaging unit 12a is arranged in an upper display region 131 and an in-vivo image B corresponding to the imaging unit 12b is arranged in a lower display region 132. In this way, a region 133' corresponding to a lesion 133 which is on the upper wall of the lumen 1a is displayed in the display region 131.

Figure 12C:
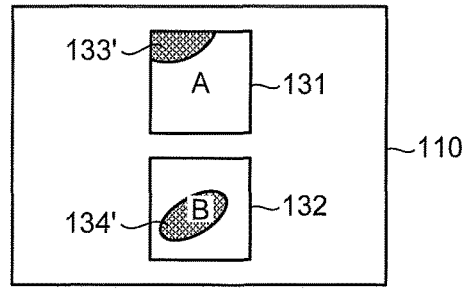

After passing through the position P31, the capsule endoscope 2 moves in the lumen 1a, with the imaging unit 12a up. In this case, as illustrated in FIG. 12C, in the image display region 110 corresponding to the position P32, the in-vivo image A corresponding to the imaging unit 12a is arranged in the upper display region 131 and the in-vivo image B corresponding to the imaging unit 12b is arranged in the lower display region 132. In this way, the region 133' corresponding to the lesion 133 which is on the upper wall of the lumen 1a is displayed in the upper display region 131 and a region 134' corresponding to a lesion 134 which is on the lower wall of the lumen 1a is displayed in the lower display region 132.

Figure 12D:
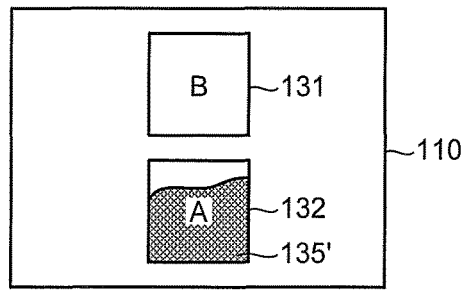

Then, the capsule endoscope 2 passes through a position P33, with the imaging unit 12b slightly up. In this case, as illustrated in FIG. 12D, in the image display region 110 corresponding to the position P33, the in-vivo image B corresponding to the imaging unit 12b is arranged in the upper display region 131 and the in-vivo image A corresponding to the imaging unit 12a is arranged in the lower display region 132. In this way, a region 135' corresponding to a lesion 135 which is on the lower wall of the lumen 1a is displayed in the lower display region 132.

As described above, according to the third embodiment, the in-vivo images to be arranged in the upper display region 131 and the lower display region 132 are determined based on the postures of the imaging units 12a and 12b. Therefore, the user can intuitively know the position (the upper side or the lower side of the lumen) of a part of interest (for example, a lesion) in the lumen in the in-vivo image.

Fourth Embodiment

Next, a fourth embodiment of the invention will be described.

The structure of a capsule endoscope system according to the fourth embodiment is the same as that illustrated in FIGS. 1 to 6. the fourth embodiment differs from the second embodiment in that, in addition to the moving direction of the capsule endoscope 2, the posture of the capsule endoscope 2 is applied to determine the arrangement of in-vivo images.

The posture determining unit 563 determines the positional relationship between imaging units 12a and 12b based on information about the posture of the capsule endoscope 2 which is associated with the image data of the in-vivo image. An imaging unit specifying unit 562 specifies the imaging unit which faces the moving direction of the capsule endoscope 2 and the imaging unit which faces the direction opposite to the moving direction at the imaging time, based on the determination result of a moving direction determining unit 561. In addition, the imaging unit specifying unit 562 specifies the imaging unit which faces up and the imaging unit which faces down, based on the determination result of the posture determining unit 563. A display control unit 57 arranges the in-vivo image captured by the imaging unit 12a which is specified to face the moving direction in a display region which is disposed in the moving direction and arranges the in-vivo image captured by the imaging unit which 12b is specified to face the direction opposite to the moving direction in a display region which is disposed in the direction opposite to the moving direction. In addition, the display control unit 57 changes the positions of the display region which is disposed in the moving direction and the display region which is disposed in the direction opposite to the moving direction in the image display region 110 in the vertical direction, based on the relative positional relationship between the imaging units in the vertical direction.

Figure 13A:
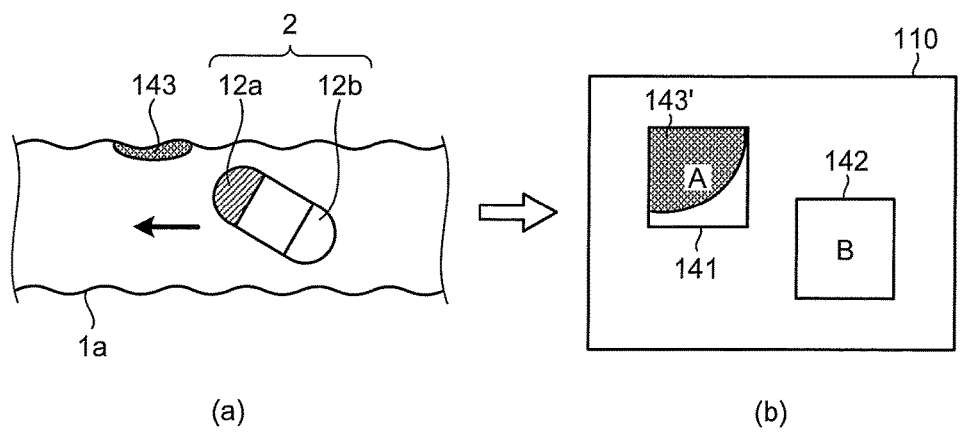
FIGS. 13A and 13B are schematic diagrams illustrating an in-vivo image display method according to a fourth embodiment.

Next, the detailed arrangement of the in-vivo images in the fourth embodiment will be described with reference to schematic diagrams. (a) of FIG. 13A illustrates an aspect in which the capsule endoscope 2 moves to the left side in the lumen 1a, with the imaging unit 12a facing to the left side of (a) of FIG. 13A. The imaging unit 12a is arranged above the imaging unit 12b. In this case, as illustrated in (b) of FIG. 13A, the in-vivo image A captured by the imaging unit 12a is arranged in a display region 141 which is disposed in the moving direction and the position of the display region 141 shifts upward in the image display region 110. Since the imaging unit 12b is arranged below the imaging unit 12a, the in-vivo image B captured by the imaging unit 12b is arranged in a display region 142 which is disposed in the direction opposite to the moving direction and the position of the display region 142 shifts downward in the image display region 110. In this way, a region 143' corresponding to a lesion 143 which is on the upper wall of the lumen 1a is displayed in the display region 141 which is disposed in the moving direction.

Figure 13B:
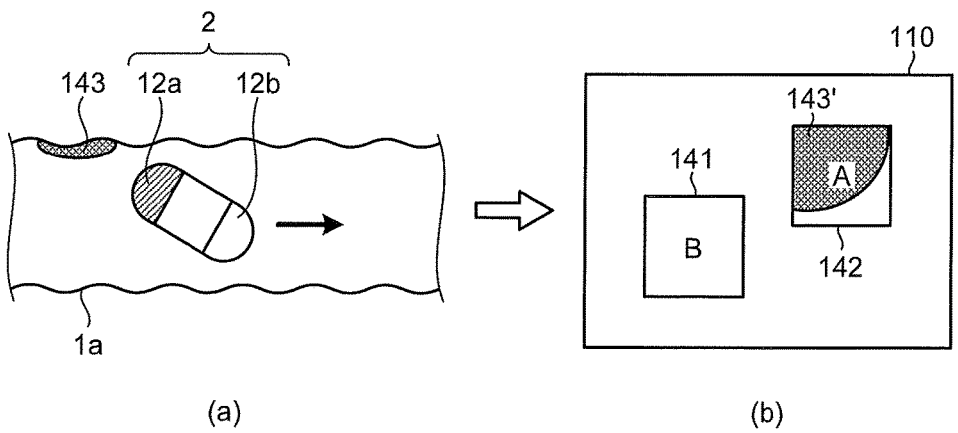

(a) of FIG. 13B illustrates an aspect in which the capsule endoscope 2 moves to the right side in the lumen 1a, with the imaging unit 12b facing to the right side of (a) of FIG. 13B. The imaging unit 12b is arranged below the imaging unit 12a. In this case, as illustrated in (b) of FIG. 13B, the in-vivo image B captured by the imaging unit 12b is displayed in the display region 141 which is disposed in the moving direction and the position of the display region 141 shifts downward in the image display region 110. Since the imaging unit 12a is arranged above the imaging unit 12b, the in-vivo image A captured by the imaging unit 12a is arranged in the display region 142 which is disposed in the direction opposite to the moving direction and the position of the display region 142 shifts upward in the image display region 110. In this way, the region 143' corresponding to the lesion 143 is displayed in the display region 142 which is disposed in the direction opposite to the moving direction.

As described above, according to the fourth embodiment, the user can visually and intuitively know the observation direction (the upper side or the lower side of the lumen 1a) with respect to the moving direction of the capsule endoscope 2.

Modification 4-1

In the fourth embodiment, the posture of the capsule endoscope 2 is applied to the display of the in-vivo image according to the moving direction of the capsule endoscope 2 which has been described in the second embodiment. However, the display of the in-vivo image to which the posture of the capsule endoscope 2 is applied may be performed for the first embodiment. Hereinafter, the detailed arrangement of in-vivo images according to Modification 4-1 will be described with reference to FIGS. 14A to 14D. In Modification 4-1, the display region 141 disposed in the moving direction (on the anus side) is set to the left side of the image display region 110 and the display region 142 disposed in the direction (on the mouth side) opposite to the moving direction is set to the right side of the image display region 110.

Figure 14A:
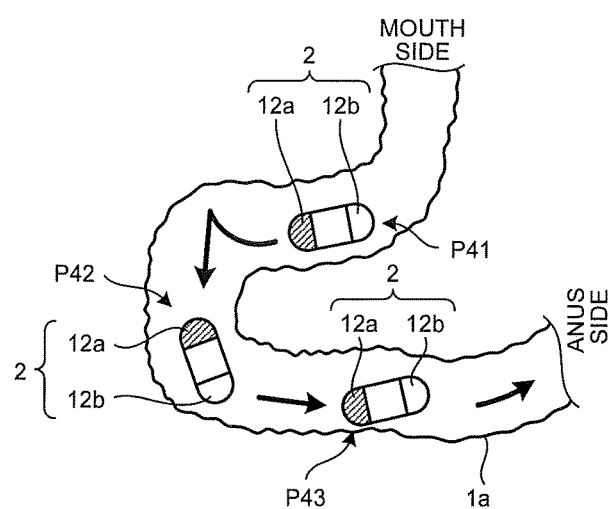
FIGS. 14A to 14D are schematic diagrams illustrating an in-vivo image display method according to Modification 4-1.
Figure 14B:
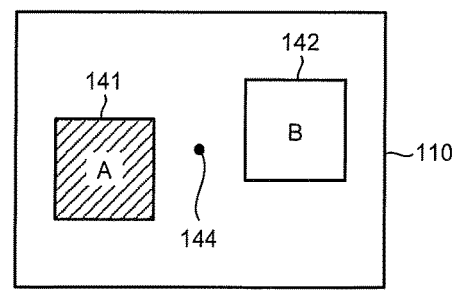

As illustrated in FIG. 14A, the capsule endoscope 2 which has passed through a position P41 moves with the imaging unit 12a facing the anus. In this case, as illustrated in FIG. 14B, the in-vivo image A captured by the imaging unit 12a is displayed in the display region 141 disposed in the moving direction and the in-vivo image B captured by the imaging unit 12b is arranged in the display region 142 disposed in the direction opposite to the moving direction. The positions of the display regions 141 and 142 are rotated and adjusted about a central axis 144 according to the positional relationship between the imaging units 12a and 12b. Specifically, the imaging unit 12a is slightly lower than the imaging unit 12b. Therefore, the positions of the display regions 141 and 142 are rotated in a counterclockwise direction about the central axis 144 such that the in-vivo image A shifts downward and the in-vivo image B shifts upward and are then set in this state.

Figure 14C:
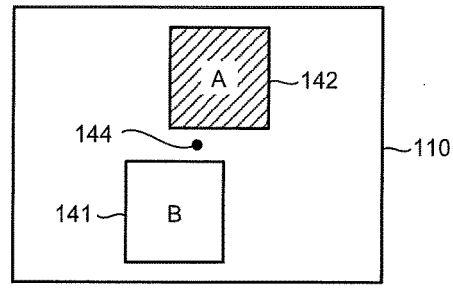

The capsule endoscope 2 which has passed through a position P42 moves with the imaging unit 12b facing the anus. In this case, as illustrated in FIG. 14C, the in-vivo image B is arranged in the display region 141 disposed in the moving direction and the in-vivo image A is arranged in the display region 142 disposed in the direction opposite to the moving direction. At the position P42, the inclination of the capsule endoscope 2 with respect to the horizontal direction is more than that at the position P41 and the difference between the positions of the imaging unit 12a and the imaging unit 12b in the vertical direction is more than that at the position P41. Therefore, the positions of the display regions 141 and 142 are greatly rotated and adjusted about the central axis 144 in the range in which the positional relationship between the display regions 141 and 142 in the horizontal direction is not reversed.

Figure 14D:
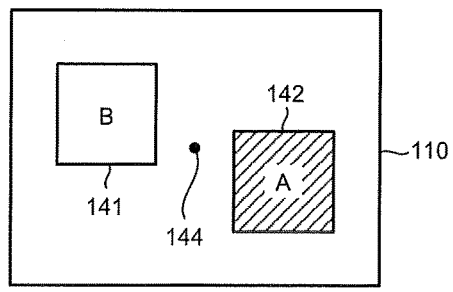

The capsule endoscope 2 which has passed through a position P43 moves with the imaging unit 12b facing the anus. In this case, as illustrated in FIG. 14D, the in-vivo image B is arranged in the display region 141 disposed in the moving direction and the in-vivo image A is arranged in the display region 142 disposed in the direction opposite to the moving direction. At the position P43, contrary to the position P42, the imaging unit 12b is arranged above the imaging unit 12a. Therefore, the positions of the display regions 141 and 142 are rotated in the clockwise direction about the central axis 144 such that the in-vivo image B shifts upward and the in-vivo image A shifts downward and are then set in this state.

Modification 4-2

The capsule endoscope system may be configured such that the user can know the local moving direction of the capsule endoscope 2 in the display of the in-vivo image based on the moving direction of the capsule endoscope 2 from the mouth to the anus of the subject 1 and the posture of the capsule endoscope 2. Next, the detailed arrangement of in-vivo images according to Modification 4-2 will be described with reference to FIGS. 15A to 15C. In Modification 4-2, the display region 141 disposed in the moving direction (on the anus side) is set on the left side of the image display region 110 and the display region 142 disposed in the direction (on the mouth side) opposite to the moving direction is set on the right side of the image display region 110.

Figure 15A:
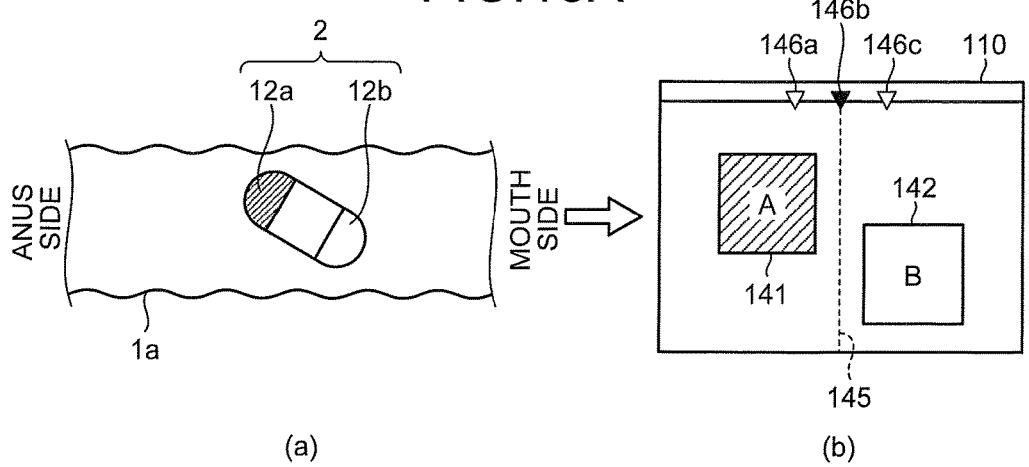
FIGS. 15A to 15C are schematic diagrams illustrating an example of the display of in-vivo images according to Modification 4-2.

(a) of FIG. 15A illustrates an aspect in which the capsule endoscope 2 stays at one point, with the imaging unit 12a facing the anus and the upper side. In this case, as illustrated in (b) of FIG. 15A, the in-vivo image captured by the imaging unit 12a is arranged in the display region 141 disposed in the moving direction and the in-vivo image captured by the imaging unit 12b is arranged in the display region 142 disposed in the direction opposite to the moving direction. In addition, the relative position of the display regions 141 and 142 in the vertical direction is determined in correspondence with the positional relationship between the imaging units 12a and 12b. In this case, in order to make the user recognize that the capsule endoscope 2 does not move in any direction, gauges 146a to 146c, which are indicators for the position of a central axis 145 between the display regions 141 and 142, may be displayed in the image display region 110. In FIG. 15A, the position of the central axis 145 corresponds to the gauge 146b which is arranged at the center of the image display region 110.

Figure 15B:
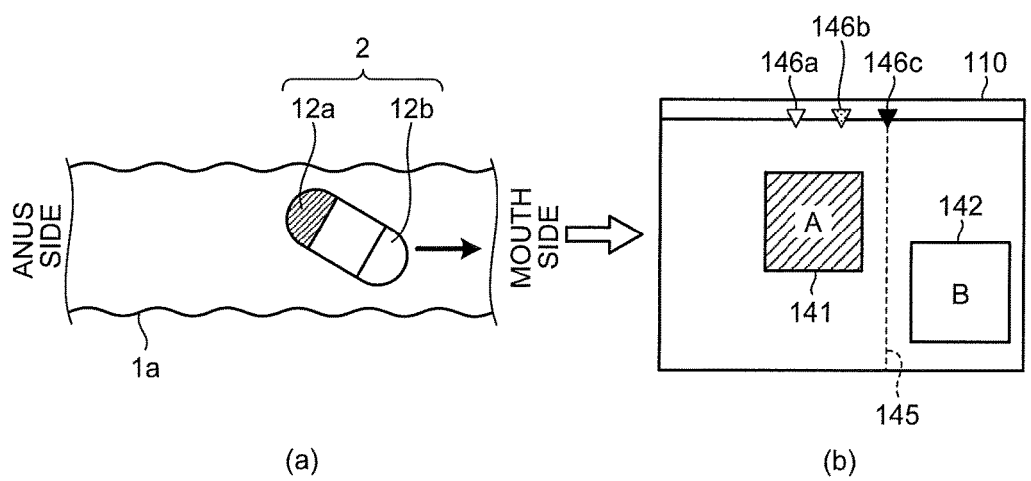

(a) of FIG. 15B illustrates an aspect in which the capsule endoscope 2 moves to the mouth, with the imaging unit 12a facing the anus and the upper side. In this case, as illustrated in (b) of FIG. 15B, the in-vivo images A and B are arranged in the display regions 141 and 142, respectively, and the positions of the display regions 141 and 142 in the vertical direction are determined in correspondence with the positional relationship between the imaging units 12a and 12b. In addition, the display regions 141 and 142 shift in a direction (to the right side of FIG. 15B) corresponding to the moving direction of the capsule endoscope 2 while maintaining the positional relationship therebetween. In this case, since the central axis 145 between the display regions 141 and 142 also shifts to the right side, the user can know the moving direction of the capsule endoscope 2 with reference to the gauges 146a to 146c. In FIG. 15B, the position of the central axis 145 corresponds to the gauge 146c which is on the right side of the center of the image display region 110. In addition, the amount of shift of the display regions 141 and 142 may be changed depending on the moving speed of the capsule endoscope 2.

Figure 15C:
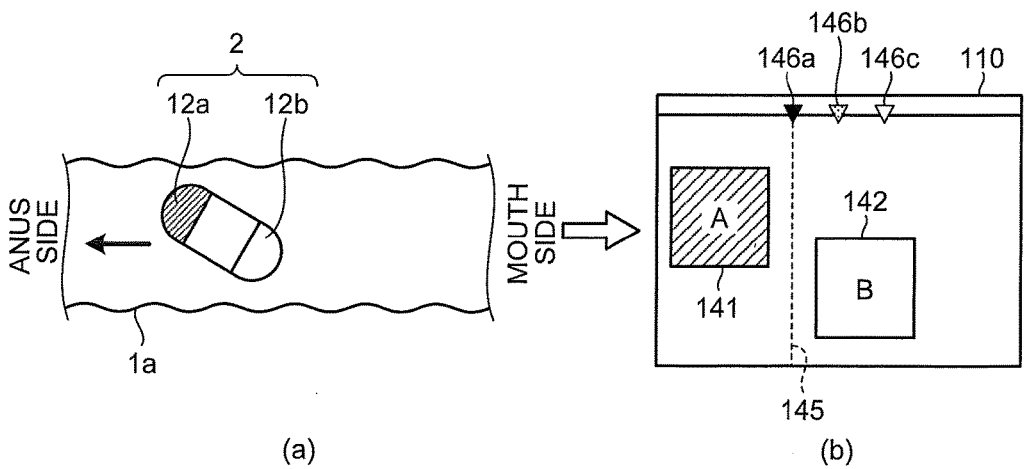

(a) of FIG. 15C illustrates an aspect in which the capsule endoscope 2 moves to the anus in the same posture as that illustrated in FIG. 15B. In this case, as illustrated in (b) of FIG. 15C, the in-vivo images A and B are arranged in the display regions 141 and 142, respectively, and the positions of the display regions 141 and 142 in the vertical direction are determined in correspondence with the positional relationship between the imaging units 12a and 12b. In addition, the display regions 141 and 142 shift in a direction (to the left side of FIG. 15C) corresponding to the moving direction of the capsule endoscope 2 while maintaining the positional relationship therebetween. In FIG. 15C, the position of the central axis 145 corresponds to the gauge 146a which is arranged on the left side of the center of the image display region 110.

According to Modification 4-2, the user can easily know the moving direction of the capsule endoscope 2 to the mouth or the anus and intuitively know the posture of the capsule endoscope 2.

Fifth Embodiment

Next, a fifth embodiment of the invention will be described.

The structure of a capsule endoscope system according to the fifth embodiment is the same as that illustrated in FIGS. 1 to 6. the fifth embodiment is characterized in that the arrangement of in-vivo images on an observation screen is determined based on coordinates in a model in which the lumen 1a of the subject 1 extends in a line.

An imaging unit specifying unit 562 specifies an imaging unit which faces a moving direction and an imaging unit which faces a direction opposite to the moving direction in a coordinate system in which the direction from the mouth to the anus of the lumen 1a is an X'-axis, based on the determination results of a moving direction determining unit 561 and a posture determining unit 563. The posture determining unit 563 determines the positional relationship between imaging units 12a and 12b based on information about the posture of the capsule endoscope 2. A display control unit 57 determines the arrangement of the in-vivo images in an image display region 110 based on the specification result of the imaging unit specifying unit 562 and the determination result of the posture determining unit 563.

Figure 16A:
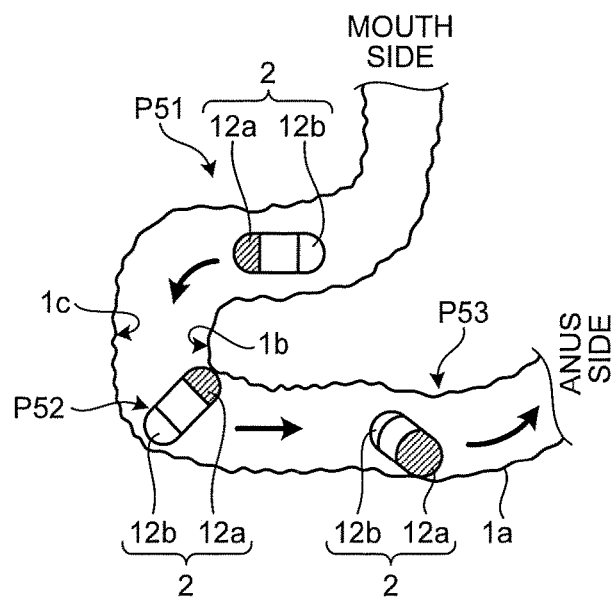
FIGS. 16A and 16B are diagrams illustrating the coordinates of a capsule endoscope according to a fifth embodiment.
Figure 16B:
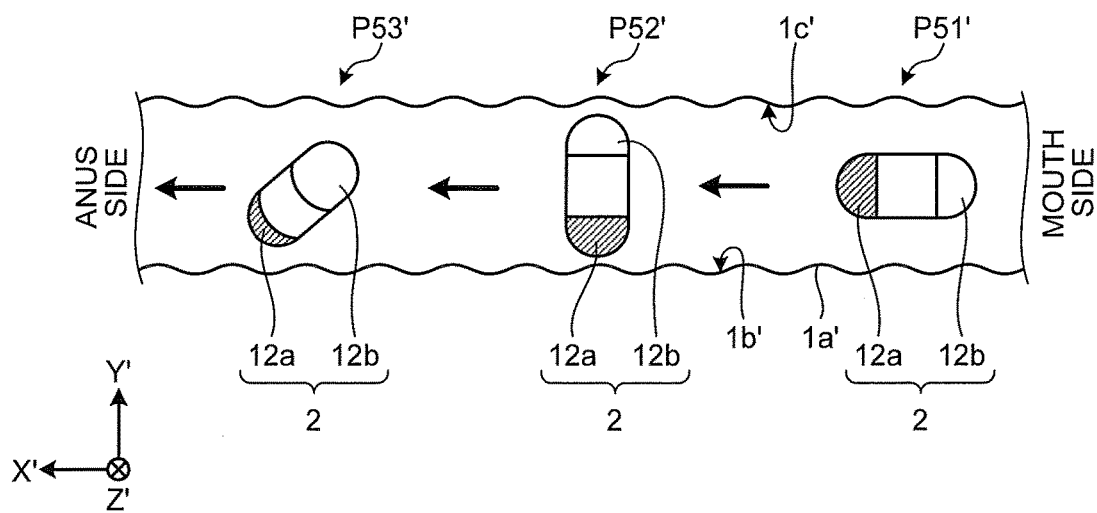

Next, the detailed arrangement of the in-vivo images in the fifth embodiment will be described with reference to schematic diagrams. FIG. 16A is a schematic diagram illustrating the capsule endoscope 2 which moves in the lumen 1a. FIG. 16B is a schematic diagram illustrating the moving direction and posture of the capsule endoscope 2 in a lumen model 1a' in which the direction of the lumen 1a from the mouth to the anus is the X'-axis. In the lumen model 1a', any two axes perpendicular to the X'-axis may be set. In FIGS. 16A and 16B, the direction parallel to the plane of paper is a Y'-axis and the direction perpendicular to the plane of paper is a Z'-axis.

Figure 17A:
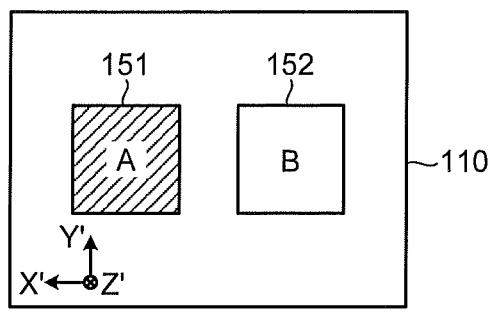
FIGS. 17A to 17C are schematic diagrams illustrating an example of the display of in-vivo images according to the fifth embodiment.
Figure 17B:
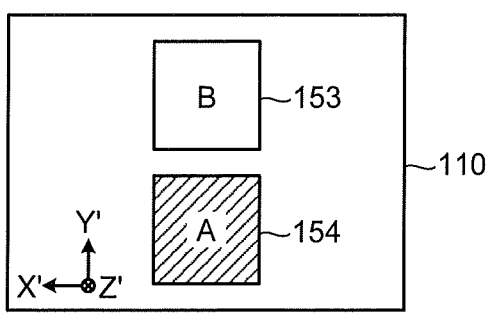
Figure 17C:
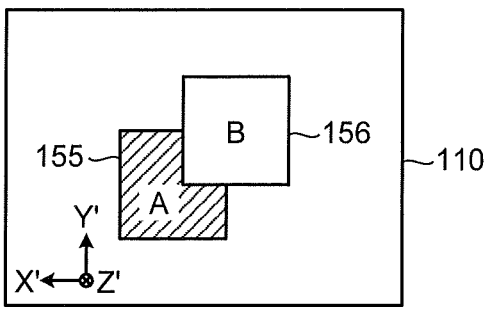

FIGS. 17A to 17C illustrate the arrangement of the in-vivo images captured at the time when the capsule endoscope 2 illustrated in FIG. 16A passes through positions P51, P52, and P53. The capsule endoscope 2 which has passed through the position P51 moves while the axis thereof is substantially parallel to the length direction of the lumen 1a and the imaging unit 12a faces the anus. Therefore, at a position P51' of the lumen model 1a' corresponding to the position P51, the capsule endoscope 2 moves with the imaging unit 12a facing the moving direction (the positive direction of the X'-axis). Therefore, as illustrated in FIG. 17A, in the image display region 110, an in-vivo image A captured by the imaging unit 12a is arranged in a display region 151 disposed in the moving direction and an in-vivo image B captured by the imaging unit 12b is disposed in a display region 152 disposed in a direction opposite to the moving direction.

The capsule endoscope 2 which has passed through the position P52 moves while the axis thereof is substantially perpendicular to the length direction of the lumen 1a, the imaging unit 12a faces an inner wall 1b, and the imaging unit 12b faces an inner wall 1c. Therefore, at a position P52' of the lumen model 1a' corresponding to the position P52, the capsule endoscope 2 moves while the imaging unit 12a faces an inner wall 1b' (the negative direction of the Y'-axis) corresponding to the inner wall 1b and the imaging unit 12b faces an inner wall 1c' (the positive direction of the Y'-axis) corresponding to the inner wall 1c. Therefore, as illustrated in FIG. 17B, the in-vivo image B captured by the imaging unit 12b is arranged in an upper display region 153 of the image display region 110 and the in-vivo image A captured by the imaging unit 12a is arranged in a lower display region 154. At the position P52, since the two imaging units do not certainly face the moving direction, the display regions 153 and 154 are vertically arranged in FIG. 17B. When any of the imaging units 12a and 12b faces the moving direction, each of the display regions 153 and 154 shifts in a predetermined direction (the right or left direction) according to the moving direction and posture of the capsule endoscope 2.

The capsule endoscope 2 which has passed through the position P53 moves with the imaging unit 12a facing the anus and the inner wall 1c. In addition, in the capsule endoscope 2, the imaging unit 12a faces the front side of the plane of paper and the imaging unit 12b faces the rear side of the plane of paper. That is, at a position P53' of the lumen model 1a' corresponding to the position P53, the capsule endoscope 2 moves while the imaging unit 12a faces the moving direction (the positive direction of the X'-axis) and the inner wall 1b' (the negative direction of the Y'-axis) corresponding to the inner wall 1b and also faces the front side of the plane of paper (the negative direction of the Z'-axis) and the imaging unit 12b faces the rear side of the plane of paper (the positive direction of the Z'-axis). Therefore, as illustrated in FIG. 17C, the in-vivo image A captured by the imaging unit 12a is arranged in a display region 155 disposed in the moving direction and the in-vivo image B captured by the imaging unit 12b is arranged in a display region 156 disposed in the direction opposite to the moving direction.

In a case in which the positions of the display regions 155 and 156 are adjusted according to the positional relationship between the imaging units 12a and 12b, when portions of or the entire display regions 155 and 156 overlap each other on the screen (that is, the coordinates of the imaging units 12a and 12b overlap each other in the X'-Y' plane), a method of overlapping the display regions 155 and 156 is determined according to the values of the Z'-axis coordinates of the imaging units 12a and 12b. For example, at the position P53', since the imaging unit 12b is disposed on the front side of the imaging unit 12a, the display region 156 in which the in-vivo image B is arranged overlaps the display region 155 in which the in-vivo image A is arranged, as illustrated in FIG. 17C.

As described above, according to the fifth embodiment, the user can intuitively and easily know the three-dimensional posture of the capsule endoscope 2 with respect to the moving direction (the direction to the anus) of the capsule endoscope 2.

Modification 5-1

Figure 18:
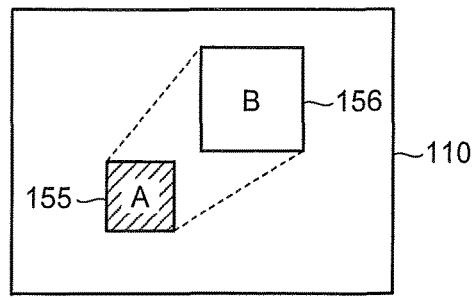
FIG. 18 is a schematic diagram illustrating an example of the display of in-vivo images according to Modification 5-1.

In the fifth embodiment, the positional relationship of the capsule endoscope 2 in the depth direction is displayed by the overlap between the display regions 155 and 156. However, various other methods may be used to the positional relationship. For example, as illustrated in FIG. 18, the display region 155 may be reduced such that the imaging unit 12a corresponding to the in-vivo image A which is arranged in the display region 155 is disposed on the rear side of the imaging unit 12b with respect to the plane of paper. On the other hand, the display region 156 may be enlarged. Alternatively, the display region 155 may be reduced and the display region 156 is enlarged.

According to Modification 5-1, it is possible to display the entire display region 155 which is arranged on the rear side on the screen.

Modification 5-2

In the lumen model 1a' described in the fifth embodiment, in some cases, the directions in which the imaging units 12a and 12b capture the in-vivo images A and B and the arrangement of the in-vivo images A and B in the image display region 110 are reversed according to the relationship between a change in the posture of the capsule endoscope 2 due to rotation and the shape of the lumen. In this case, the direction of the Y'-axis in the lumen model 1a' may be appropriately changed to match the positional relationship between the imaging units 12a and 12b at the imaging time with the positional relationship between the in-vivo images A and B during display.

Specifically, when the posture determining unit 563 detects, for example, the reversal of the capsule endoscope 2 in the Y'-axis direction from information about the posture of the capsule endoscope 2, the display control unit 57 switches the in-vivo images displayed in the display regions 153 and 154 based on the position detected by the posture determining unit 563.

Figure 19A:
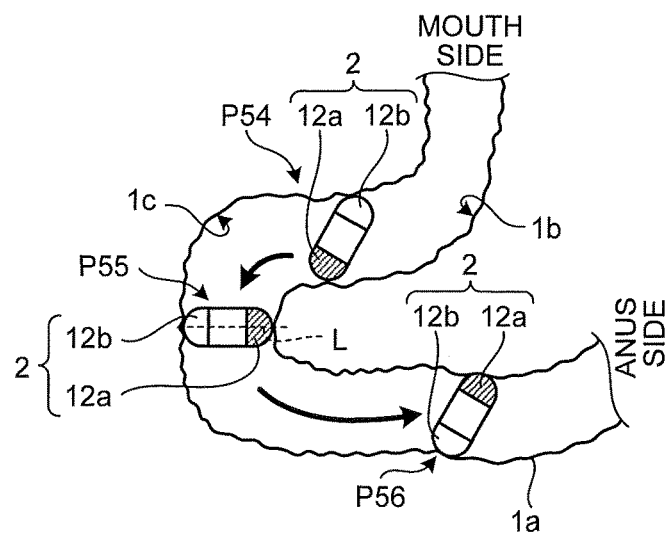
FIGS. 19A to 19C are schematic diagrams illustrating an in-vivo image display method according to Modification 5-2.
Figure 19B:
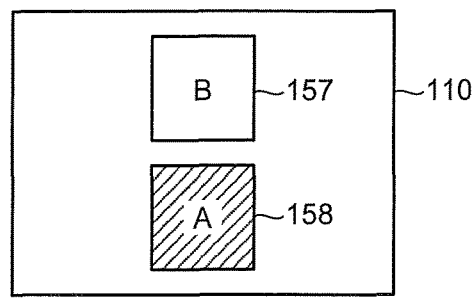

For example, as illustrated in FIG. 19A, the capsule endoscope 2 which has passed through a position P54 moves with the imaging unit 12a facing the inner wall 1b. Therefore, when the in-vivo images A and B are displayed based on the coordinates in the lumen model 1a', the in-vivo image B is arranged in an upper display region 157 and the in-vivo image A is arranged in a lower display region 158, as illustrated in FIG. 19B.

Then, when the capsule endoscope 2 rotates and reaches a position P56 through a position P55, the imaging unit 12a faces the inner wall 1b, similar to the position P54. Therefore, when the in-vivo images A and B are displayed based on the coordinates in the lumen model 1a', the positional relationship between the in-vivo images A and B on the image display region 110 and the positional relationship between the imaging units 12a and 12b at the position P56 are reversed.

Figure 19C:
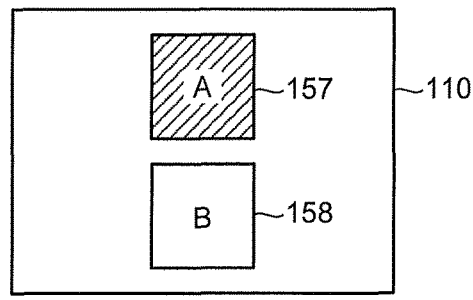

When the capsule endoscope 2 rotates, the Y'-axis direction in the lumen model 1a' is reversed at the time when the axis L is horizontal (that is, at the time of the position P55). Then, as illustrated in FIG. 19C, the in-vivo image A is arranged in the upper display region 157 and the in-vivo image B is arranged in the lower display region 158. Therefore, it is possible to match the positional relationship between the imaging units 12a and 12b at the position P56 with the positional relationship between the in-vivo images A and B in the image display region 110.

Sixth Embodiment

Next, a sixth embodiment of the invention will be described.

The structure of a capsule endoscope system according to the sixth embodiment is the same as that illustrated in FIGS. 1 to 6. the sixth embodiment is characterized in that the arrangement of in-vivo images on an observation screen is determined based on the coordinates based on the subject 1.

Figure 20A:
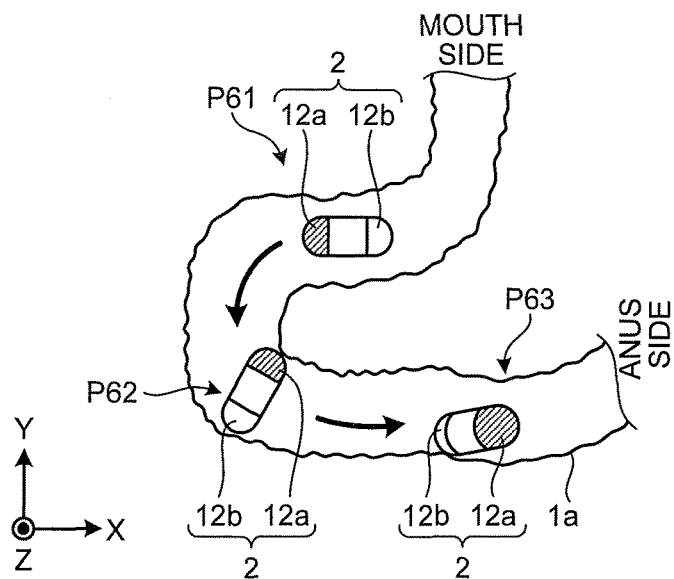
FIGS. 20A and 20B are diagrams illustrating the coordinates of a capsule endoscope according to a sixth embodiment.
Figure 20B:
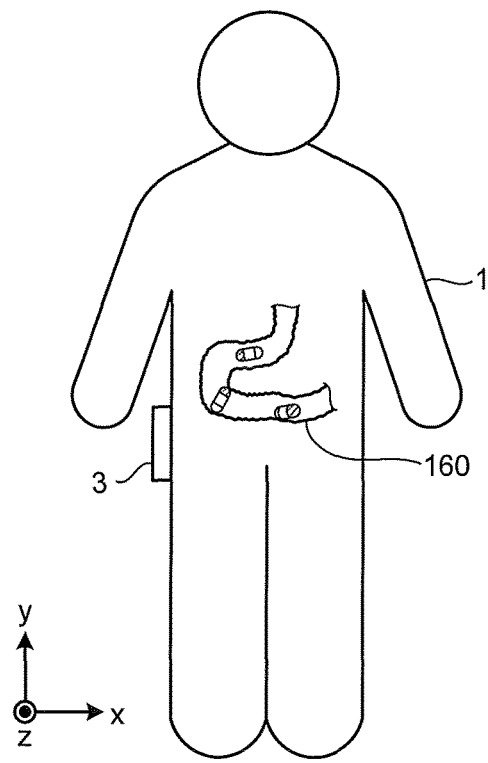

In this case, a posture determining unit 563 detects the posture of a capsule endoscope 2 at the coordinates (absolute coordinates (X, Y, Z)) based on gravity acceleration, based on posture information (see FIG. 20A). In addition, the posture determining unit 563 determines the posture of the subject 1, based on the information about the posture of the subject 1 which is generated based on a signal detected by the gyro sensor 37 provided in the receiving device 3 of the subject 1 (see FIG. 20B). The posture determining unit 563 calculates the relative coordinates (relative coordinates (x, y, z)) of the capsule endoscope 2 with respect to the subject 1 from the posture of the capsule endoscope 2 at the absolute coordinates and the posture of the subject 1. An intraluminal model 160 based on the subject 1 illustrated in FIG. 20B is acquired based on the relative coordinates. When the subject 1 is standing, the absolute coordinates are identical to the relative coordinates. When the subject 1 is lying on the side, the plane formed by two axes in the absolute coordinates is rotated 90 degrees to convert the absolute coordinates into the relative coordinates.

The display control unit 57 determines the arrangement of in-vivo images A and B captured by imaging units 12a and 12b based on the moving direction of the capsule endoscope 2 and the positional relationship between the imaging units 12a and 12b in the intraluminal model 160 acquired by the posture determining unit 563.

For example, the capsule endoscope 2 which has passed through a position P61 moves with the imaging unit 12a facing the moving direction (the anus). Therefore, in an image display region 110 illustrated in FIG. 21A, the in-vivo image A is arranged in a display region 161 disposed in the moving direction and the in-vivo image B is arranged in a display region 162 disposed in a direction opposite to the moving direction.

The capsule endoscope 2 which has passed through a position P62 moves with the imaging unit 12a up. Therefore, in the image display region 110 illustrated in FIG. 21B, the in-vivo image A is arranged in an upper display region 163 and the in-vivo image B is arranged in a lower display region 164. In this case, the in-vivo image arranged in the upper display region 163 corresponds to the upper wall of the lumen 1a and the in-vivo image arranged in the lower display region 164 corresponds to the lower wall of the lumen 1a.

The capsule endoscope 2 which has passed through a position P63 moves with the imaging unit 12a facing the front side of the plane of the drawing. Therefore, in the image display region 110 illustrated in FIG. 21C, the in-vivo image A is arranged in a front display region 165 and the in-vivo image B is arranged in a rear display region 166. In this case, for example, the front display region 165 corresponds to the abdomen of the subject 1 and the rear display region 166 corresponds to the back of the subject 1.

As described above, according to the sixth embodiment, the arrangement of the in-vivo images is determined based on the relative moving direction or posture of the capsule endoscope 2 in the body of the subject 1. Therefore, the user can three-dimensionally and intuitively know the observation position and direction of a part of the body of the subject 1 in the in-vivo image.

In addition, in the sixth embodiment, the front display region is superimposed on the rear display region. However, similarly to Modification 5-1, the front display region may be enlarged or the rear display region may be reduced. Alternatively, the front display region may be enlarged and the rear display region may be reduced.

Modification 6-1

In the sixth embodiment, the posture of the subject 1 is determined based on the signal detected by the gyro sensor 37 provided in the receiving device 3. However, the subject 1 may input information about the posture of the subject 1, such as standing or recumbence. In this case, the receiving device 3 may be provided with a posture input unit which is used by the patient to input the posture information. The posture input unit may be implemented by, for example, a touch panel or operation buttons.

When the subject 1 changes the posture during examination using the capsule endoscope 2 and inputs information about the current posture (posture information such as information about standing or recumbence) using the posture input unit, the signal processing unit 32 associates the input posture information with the image data received at that time. Then, the image display 5 can acquire the image data and information about the posture of the patient when the in-vivo image is captured.

Modification 6-2

The position information of the capsule endoscope 2 which is separately estimated may be displayed on the screen which is generated and displayed in the sixth embodiment. In this case, for example, the control unit 56 estimates the position of the capsule endoscope 2 at the time when each in-vivo image is captured, based on information about the reception intensity of the receiving antennas 30a to 30h which is associated with the image data. Various known methods may be used as a position estimation method. In addition, the control unit 56 may convert the coordinates of the estimated position of the capsule endoscope 2 into values on the relative coordinates calculated by the posture determining unit 563.

The display control unit 57 displays the calculated position of the capsule endoscope 2 on the image display region 110.

Figure 21A:
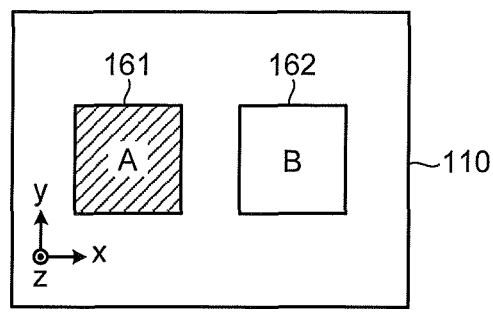
FIGS. 21A to 21C are schematic diagrams illustrating an example of the display of in-vivo images according to the sixth embodiment.
Figure 21B:
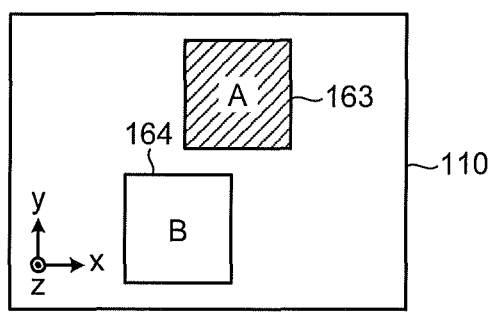
Figure 21C:
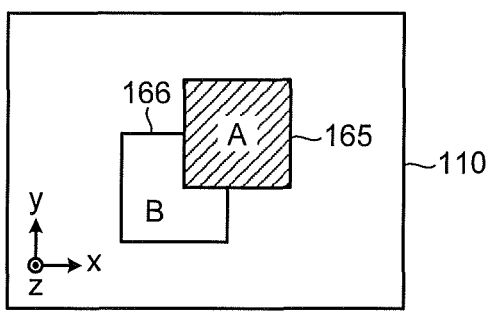
Figure 22A:
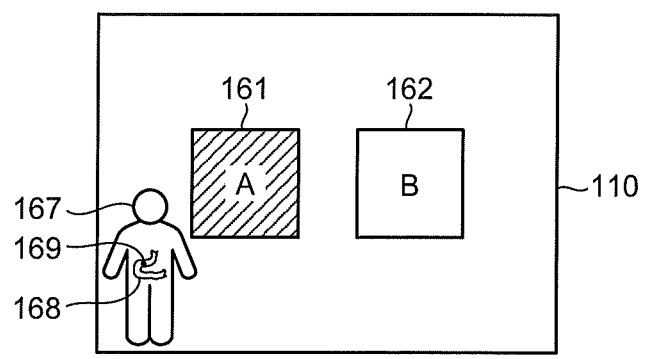
FIGS. 22A to 22C are schematic diagrams illustrating an example of the display of in-vivo images according to Modification 6-2.
Figure 22B:
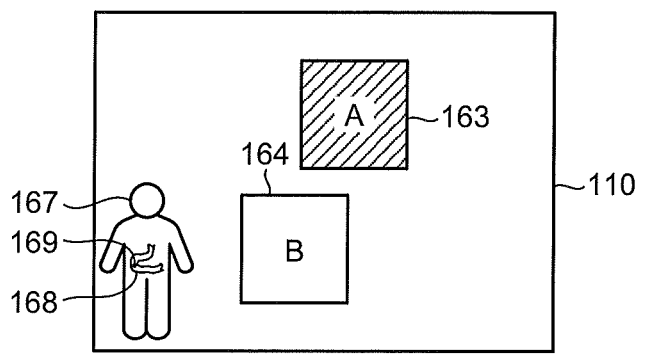
Figure 22C:
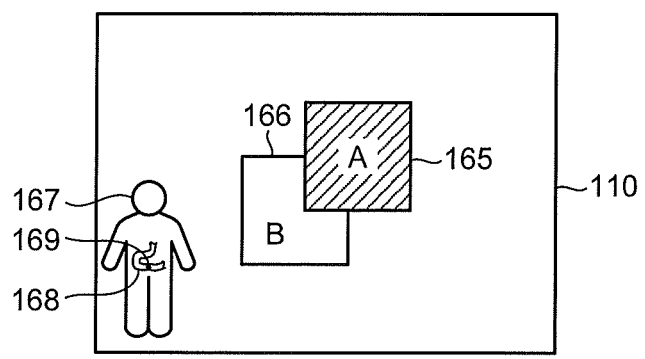

FIGS. 22A to 22C are schematic diagrams illustrating examples of the display of the in-vivo images according to Modification 6-2 and are different from FIGS. 21A to 21C in that a human body model 167 is added. A reduced FIG. 168 of the intraluminal model 160 illustrated in FIG. 20B is drawn in the human body model 167. The position of the capsule endoscope 2 corresponding to the time when the in-vivo image which is being displayed in the image display region 110 is captured is represented by a dot 169 on the reduced FIG. 168.

The user can observe the in-vivo images arranged in the display regions 161 to 166 while referring to the position of the capsule endoscope 2 on the human body model 167 to easily and intuitively know the capture position and direction of the in-vivo image which is currently being displayed in the body of the subject 1.

Seventh Embodiment

Next, a seventh embodiment of the invention will be described.

In the first to sixth embodiments, the moving direction or posture of the capsule endoscope 2 is shown by the position (for example the left, right, upper, and lower sides) of the display region or the overlapping method. However, other methods may be used to show the moving direction or posture of the capsule endoscope 2. The structure of a capsule endoscope system according to the seventh embodiment is the same as that illustrated in FIGS. 1 to 6.

Figure 23A:
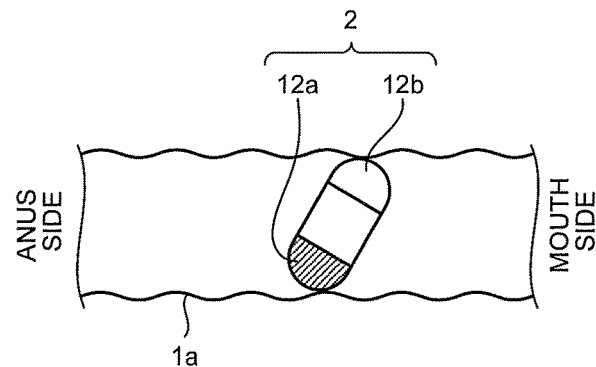
FIGS. 23A to 23C are schematic diagrams illustrating a first display example of in-vivo images according to a seventh embodiment.
Figure 23B:
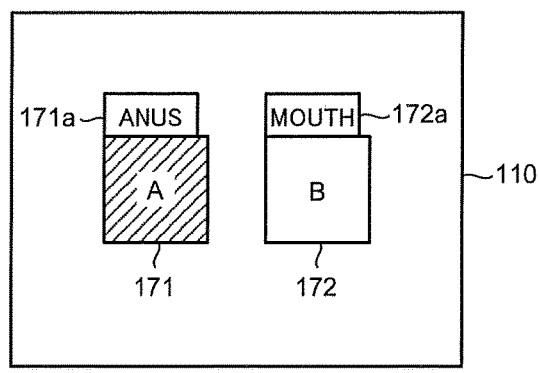
Figure 23C:
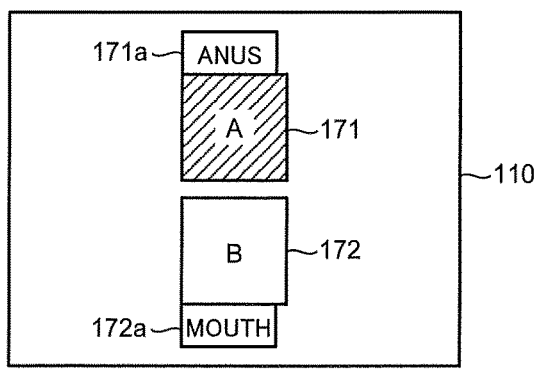

For example, as illustrated in FIGS. 23A to 23C, when an in-vivo image on the anus side of the capsule endoscope 2 is arranged in a display region 171 and an in-vivo image on the mouth side of the capsule endoscope 2 is arranged in a display region 172, an icon 171a indicating the anus side and an icon 172a indicating the mouth side may be displayed in the vicinity of the display regions 171 and 172, respectively. In this case, it is possible to improve flexibility in the arrangement of the display regions 171 and 172. For example, the display regions 171 and 172 may be laterally arranged as illustrated in FIG. 23B, or the display regions 171 and 172 may be longitudinally arranged as illustrated in FIG. 23C.

Figure 24A:
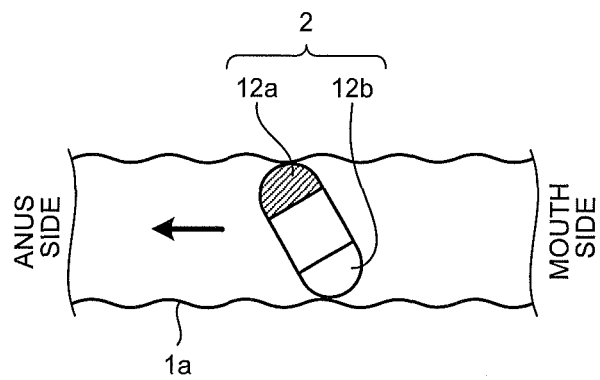
FIGS. 24A to 24C are schematic diagrams illustrating a second display example of the in-vivo images according to the seventh embodiment.
Figure 24B:
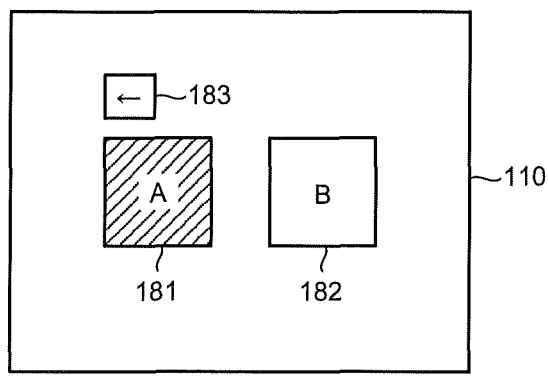
Figure 24C:
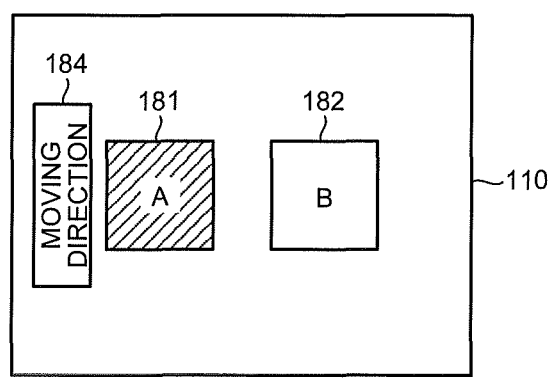

As illustrated in FIGS. 24A to 24C, when an in-vivo image corresponding to the moving direction of the capsule endoscope 2 is arranged in a display region 181 and an in-vivo image corresponding to a direction opposite to the moving direction of the capsule endoscope 2 is arranged in a display region 182, icons 183 and 184 indicating the moving direction may be displayed in the vicinity of the display region 181. In this case, the user can clearly know the display region 181 in which the in-vivo image corresponding to the moving direction of the capsule endoscope 2 is arranged.

Figure 25A:
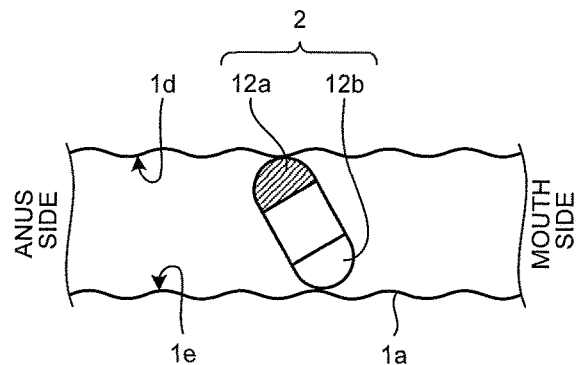
FIGS. 25A to 25C are schematic diagrams illustrating a third display example of the in-vivo images according to the seventh embodiment.
Figure 25B:
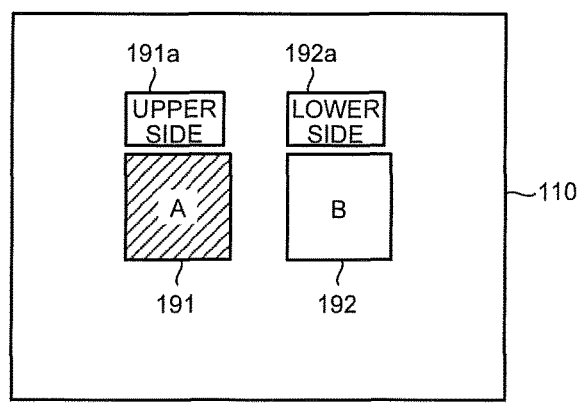
Figure 25C:
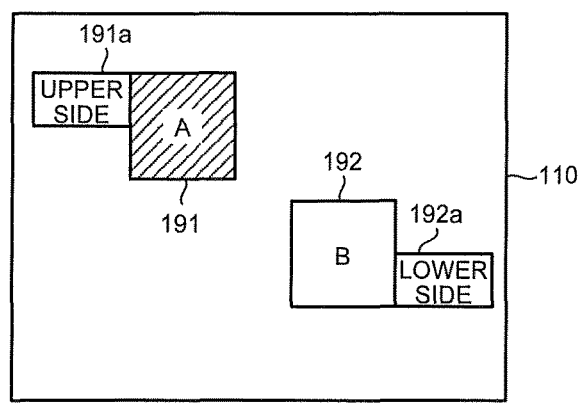

As illustrated in FIGS. 25A to 25C, when an in-vivo image on the side of an upper wall 1d is arranged in a display region 191 and an in-vivo image on the side of a lower wall 1e is arranged in a display region 192, an icon 191a indicating the upper wall 1d and an icon 192a indicating the lower wall 1e may be displayed in the vicinity of the display regions 191 and 192, respectively. In this way, it is possible to improve flexibility in the arrangement of the display regions 191 and 192. In this case, as illustrated in FIG. 25C, the positions of the display regions 191 and 192 may be adjusted according to the positional relationship between imaging units 12a and 12b which capture the in-vivo images arranged in each display region, in addition to the display of the icons 191a, 192a. In this case, the user can clearly and intuitively know the directions (for example, the upper and lower sides) indicated by the in-vivo images which are arranged in the display regions 191 and 192.

In the first to seventh embodiments, the display of the in-vivo images acquired by the capsule endoscope including two imaging units has been described. However, the first to seventh embodiments may be applied to a capsule endoscope including three or more imaging units.

the first to seventh embodiments of the invention are just illustrative, but the invention is not limited to the embodiments. Various modifications of the invention can be made according to, for example, the specifications and it will be apparent from the above description that various other embodiments can be made without departing from the scope and spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope system comprising:
a capsule endoscope configured to pass through a position within a subject, wherein the capsule endoscope comprises:
   a first image sensor configured to capture, at the position, an image in a first imaging direction; and
   a second image sensor configured to capture, at the position, an image in a second imaging direction different from the first imaging direction; and
a processor comprising hardware, wherein the processor is configured to:
   determine a moving direction in which the capsule endoscope at the position, is moving;
   determine one of the first image sensor and second image sensor as facing the moving direction, and the other of the first image sensor and the second image sensor as not facing the moving direction;
   determine a positional relationship between the first image sensor and the second image sensor with respect to a first predetermined coordinate axis, at the position within the subject;
   determine:
      a first display region position of a first display region on a display screen, wherein the first display region corresponds to the moving direction; and
      a second display region position of a second display region on the display screen, wherein the second display region does not correspond to the moving direction,
      wherein the first display region position and the second display region position are determined such that a positional relationship between the first display region position and the second display region position with respect to a second predetermined coordinate axis within the display screen matches the positional relationship between the first image sensor and the second image sensor with respect to the first predetermined coordinate axis; and
   control the display screen to display:
      within the first display region at the first display region position, the image captured by the one of the first image sensor and the second image sensor determined as facing the moving direction; and
      within the second display region at the second display region position, the image captured by the other of the first image sensor and the second image sensor determined as not facing the moving direction.

2. The capsule endoscope system according to claim 1, wherein the processor is configured to:
   calculate an amount of movement of the capsule endo scope based on a plurality of images captured at different times by at least one of the first image sensor and the second image sensor; and
   determine the moving direction based on the amount of movement of the capsule endoscope calculated.

3. The capsule endoscope system according to claim 1, wherein the positional relationship between the first image sensor and the second image sensor is a relative positional relationship between the first image sensor and second image sensor in a vertical direction with respect to the first predetermined coordinate axis.

4. The capsule endoscope system according to claim 1, wherein the processor is configured to determine the first display region position of the first display region and the second display region position of the second display region such that the first display region position and the second display region position are arranged at symmetric positions with respect to a predetermined point in the display screen.

5. The capsule endoscope system according to claim 1, wherein the second imaging direction is opposite to the first imaging direction.

6. The capsule endoscope system according to claim 1, wherein the processor is configured to determine a posture of the capsule endo scope.

* * * * *